United States Patent
Yu et al.

(10) Patent No.: US 11,959,121 B2
(45) Date of Patent: *Apr. 16, 2024

(54) SENSORS, METHODS AND KITS FOR DETECTING NADPH BASED ON RESONANCE ENERGY TRANSFER

(71) Applicant: Max-Planck-Gesellschaft zur Förderung der Wissenschaften e. V., Munich (DE)

(72) Inventors: Qiuliyang Yu, Lausanne (CH); Kai Peter Johnsson, Heidelberg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 315 days.

This patent is subject to a terminal disclaimer.

(21) Appl. No.: 16/618,610

(22) PCT Filed: May 29, 2018

(86) PCT No.: PCT/EP2018/064076
§ 371 (c)(1),
(2) Date: Dec. 2, 2019

(87) PCT Pub. No.: WO2018/219953
PCT Pub. Date: Dec. 6, 2018

(65) Prior Publication Data
US 2020/0181673 A1   Jun. 11, 2020

(30) Foreign Application Priority Data

May 30, 2017   (EP) ..................... 17173534

(51) Int. Cl.
- *C12Q 1/00* (2006.01)
- *C07K 5/10* (2006.01)
- *C12N 9/06* (2006.01)
- *C12Q 1/26* (2006.01)
- *G01N 21/76* (2006.01)

(52) U.S. Cl.
CPC ............. *C12Q 1/008* (2013.01); *C07K 5/10* (2013.01); *C12N 9/003* (2013.01); *C12Q 1/26* (2013.01); *C12Y 105/01003* (2013.01); *G01N 21/763* (2013.01); *C07K 2319/60* (2013.01); *C07K 2319/61* (2013.01)

(58) Field of Classification Search
None
See application file for complete search history.

(56) References Cited

FOREIGN PATENT DOCUMENTS

| | | | | |
|---|---|---|---|---|
| WO | WO-2015007317 A1 | * | 1/2015 | ........... G01N 21/763 |
| WO | 2016/131833 A1 | | 8/2016 | |

OTHER PUBLICATIONS

Arts, R., et al. 2017 Methods in Enzymology 589: 87-114. (Year: 2017).*
England, C.G., et al. 2016 Bioconjug Chem 27(5): 1175-1187. (HHS Public Access copy 29 pages total). (Year: 2016).*
Adams, J., et al. 1989 Biochemistry 28: 6611-6618. (Year: 1989).*
Volpato, J.P., et al. 2009 Drug Resistance Updates 12: 28-41. (Year: 2009).*
Zhao, J. et al., "Self-Assembling NanoLuc Luciferase Fragments as Probes for Protein Aggregation in Living Cells", ACS Chemical Biology, (2016), 11, pp. 132-138.
Griss, R. et al., "Bioluminescent sensor proteins for point-of-care therapeutic drug monitoring", Nature Chemical Biology, vol. 10, No. 7, Jul. 2014, pp. 598-603.
Schena, A. et al., "Modulating protein activity using tethered ligands with mutually exclusive binding sites", Nature Communications, vol. 6, (2015), 8 pgs.

* cited by examiner

*Primary Examiner* — Marsha Tsay
(74) *Attorney, Agent, or Firm* — Verrill Dana, LLP

(57) ABSTRACT

The invention relates to the detection of the cofactor reduced nicotinamide adenine dinucleotide phosphate (NADPH). Provided is a sensor molecule for the resonance energy transfer (RET)-based detection of NADPH, the sensor comprising a segment A connected via a linker to a segment B, wherein each of segment A and segment B comprises a member of a RET pair comprising a donor moiety and an acceptor moiety, further characterized in that (i) segment A comprises a binding protein (BP) for NADPH, the BP being dihydrofolate reductase (DHFR; EC 1.5.1.3) or a functional homolog, fragment, derivative or variant thereof, showing the desired NADPH binding properties, and wherein the BP comprises a heterologous protein domain inserted at or replacing at least part of the region corresponding to positions (20) to (27) of *E. coli* DHFR, said heterologous protein domain comprising the member of the RET pair; (ii) segment B comprises a ligand (L) capable of intramolecular binding to said BP only in the presence of NADPH; such that the donor moiety and the acceptor moiety are in a suitable juxtaposition to yield a RET signal when L is bound to BP, and wherein NADPH-induced binding of L to BP results in an increase in RET efficiency.

20 Claims, 12 Drawing Sheets

Figure 2A:
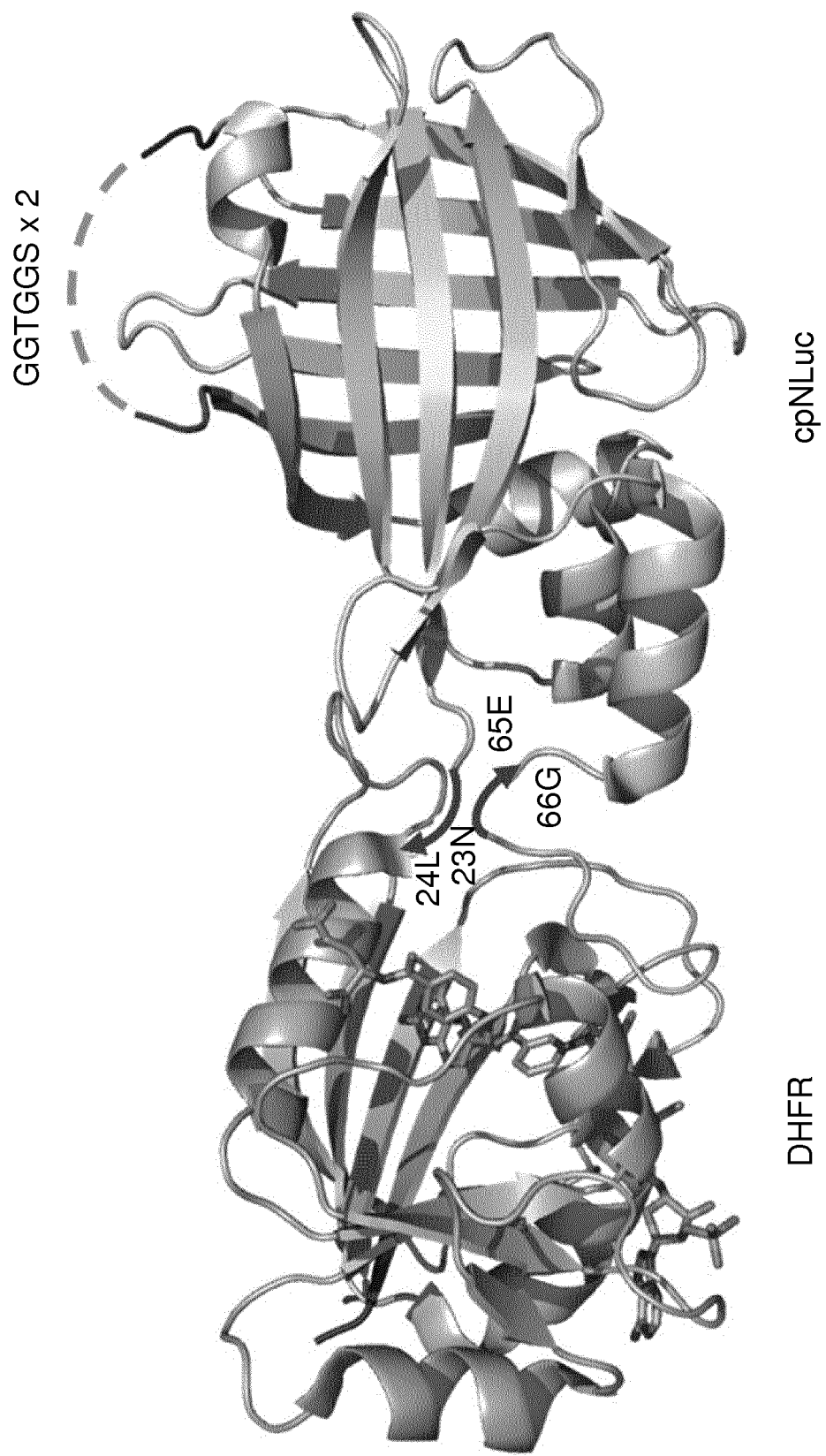

Specification includes a Sequence Listing.

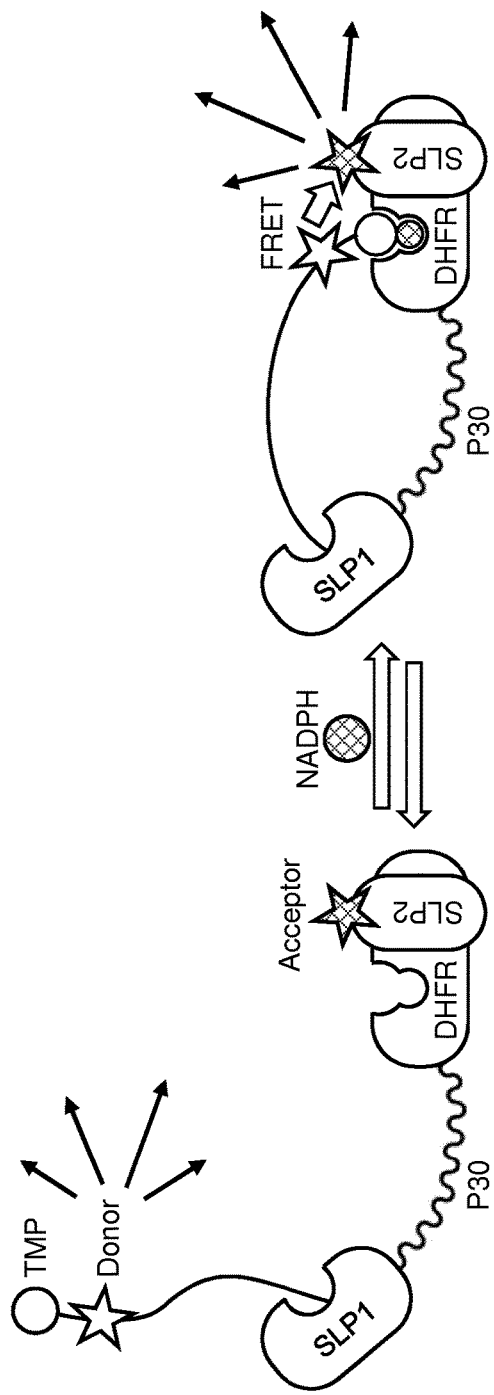
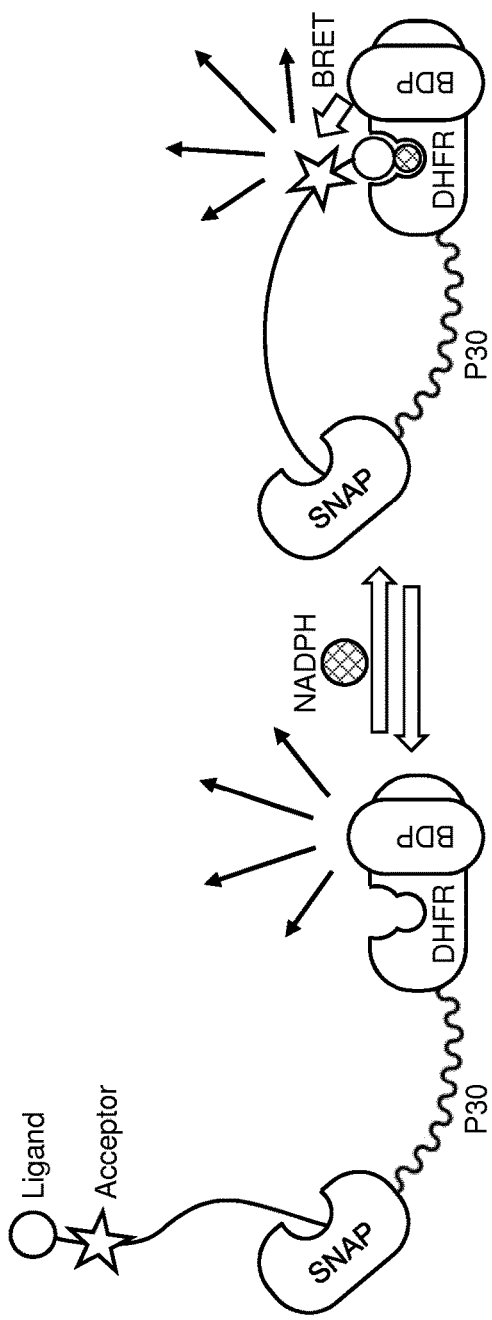
Fig. 1A
Fig. 1B

| | | | |
|---|---|---|---|
| DYR_ECOLI | P0AB04 | 1 | ---MISLIAALAVDRVIGMENAMPW-NLPADLAWFKRNTLNK------PVINGRHTWESI----GRPLPGRKNIILSSQ- | 65 |
| DYR_HUMAN | P00374 | 1 | mVGSLNCIVAVSQNMGIGKNGDLPWpPLRNEFRYFQRMTTTSSVEGKQNLVIMGKKTWFSIPEKNRPLKGRINLVLSREL | 80 |
| DYR_CHICK | P00378 | 1 | -VRSLNSIVAVCQNMGIGKGNLPWpPLRNEYKYFQRMTSTSHVEGKQNAVIMGKKTWFSIPEKNRPLKDRINIVLSREL | 79 |
| DYR_DROME | P17719 | 1 | -MLRFNLIVAVCENFGIGIRGDLPW-RIKSELKYFSRTTKRTSDPTKQNAVVMGRKTYFGVPESKRPLPDRLNIVLSTTL | 78 |
| DYR_LACCA | P00381 | 1 | ---MTAFLWAQDRDGLIGKDGHLPW-HLPDDLHYFRAQTVGK-------IMVGRRTYESFP--KRPLPERTNVWLTHQ- | 66 |

| | | | |
|---|---|---|---|
| DYR_ECOLI | P0AB04 | 66 | -PG--TDDRVTWVKSVDEAIAAC------GDVPEIMVIGGGRVYEQFLPKA--QKLYLTHIDAEVEGDTHFPDYEPDDWE | 134 |
| DYR_HUMAN | P00374 | 81 | KEP--PQGAHFLSRSLDDALKLTEQpeIANKVDMVWIVGGSSVYKEAMNHPGHLKLFVTRIMQDFESDTFFPEIDLEKYK | 158 |
| DYR_CHICK | P00378 | 80 | KEA--PKGAHYLSKSLDDALALLDSpeIKSKVDMVWIVGGTAVYKAAMEKPINHRLFVTRILHEFESDTFFPEIDYKDFK | 157 |
| DYR_DROME | P17719 | 79 | QESdlPKG-VLLCPNLETAMKILEE---QNEVENIWIVGGSGVYEEAMASPRCHRLYITKIMQKFDCDTFFPAI-PDSFR | 153 |
| DYR_LACCA | P00381 | 67 | -EDyqAQG-AVVVHDVAAVFAYAKQ----HPDQELVIAGGAQIFTAFKDDV--DTLLVTRLAGSFEGDTKMIPLNwDDFT | 138 |

| | | | |
|---|---|---|---|
| DYR_ECOLI | P0AB04 | 135 | SVFSEFHD--ADAQNSHS--YCFEILERR---- | 159 |
| DYR_HUMAN | P00374 | 159 | LL-PEYPGVLSDVQEEKGIKYKFEVYEKN---d | 187 |
| DYR_CHICK | P00378 | 158 | LL-TEYPGVPADIQEEDGIQYKFEVYQKSVlaq | 189 |
| DYR_DROME | P17719 | 154 | EV-APDSDMPLGVQEENGIKFEYKILEKHS--- | 182 |
| DYR_LACCA | P00381 | 139 | KV-----SSRTVEDTNPALTHTYEVWQKKA--- | 163 |

Fig. 2B

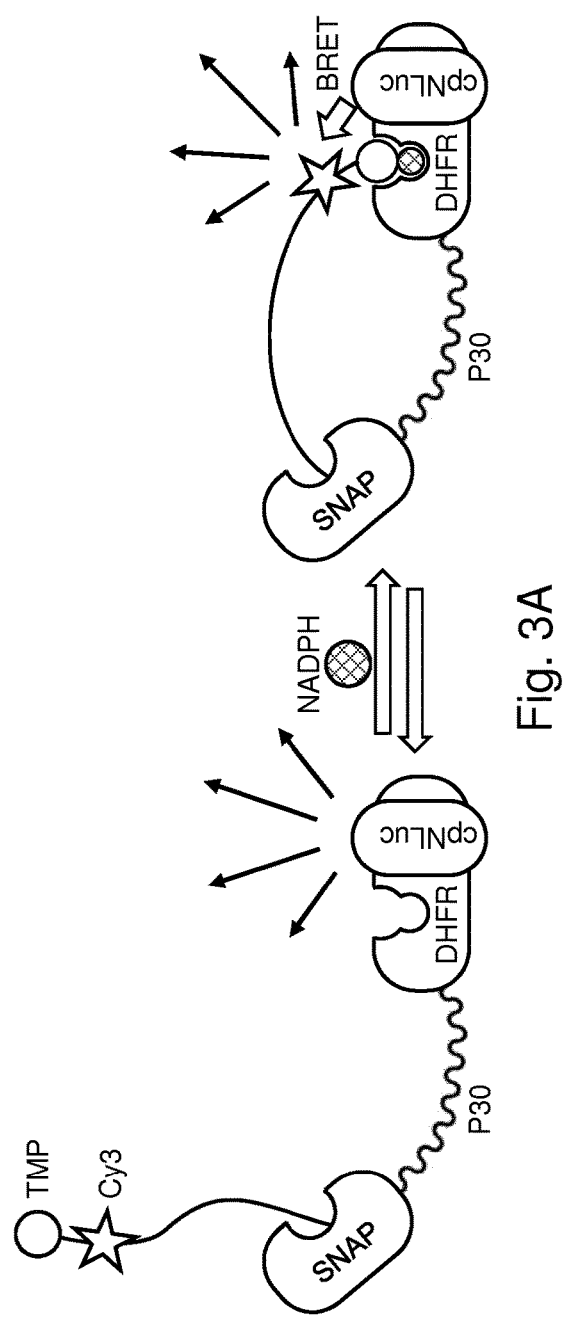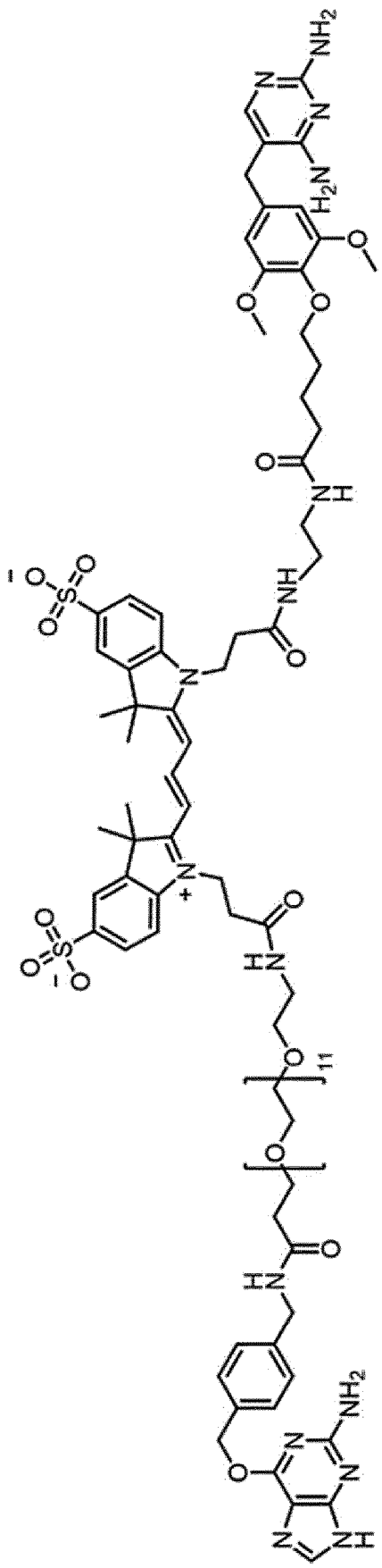
Fig. 3A
Fig. 3B

SEQUENCE LISTING

<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: linker

<400> SEQUENCE: 1

Gly Gly Thr Gly Gly Ser Gly Gly Thr Gly Gly Ser Gly Gly Ser
1               5                   10                  15

<210> SEQ ID NO 2
<211> LENGTH: 159
<212> TYPE: PRT
<213> ORGANISM: Escherichia coli

<400> SEQUENCE: 2

Met Ile Ser Leu Ile Ala Ala Leu Ala Val Asp Arg Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
           50                  55                  60

Gln Pro Gly Thr Asp Asp Arg Val Thr Trp Val Lys Ser Val Asp Glu
 65                  70                  75                  80

Ala Ile Ala Ala Cys Gly Asp Val Pro Glu Ile Met Val Ile Gly Gly
               85                  90                  95

Gly Arg Val Tyr Glu Gln Phe Leu Pro Lys Ala Gln Lys Leu Tyr Leu
           100                 105                 110

Thr His Ile Asp Ala Glu Val Glu Gly Asp Thr His Phe Pro Asp Tyr
           115                 120                 125

Glu Pro Asp Asp Trp Glu Ser Val Phe Ser Glu Phe His Asp Ala Asp
           130                 135                 140

Ala Gln Asn Ser His Ser Tyr Cys Phe Glu Ile Leu Glu Arg Arg
145                 150                 155

<210> SEQ ID NO 3
<211> LENGTH: 187
<212> TYPE: PRT
<213> ORGANISM: Homo sapiens

<400> SEQUENCE: 3

Met Val Gly Ser Leu Asn Cys Ile Val Ala Val Ser Gln Asn Met Gly
 1               5                  10                  15

Ile Gly Lys Asn Gly Asp Leu Pro Trp Pro Leu Arg Asn Glu Phe
            20                  25                  30

Arg Tyr Phe Gln Arg Met Thr Thr Thr Ser Ser Val Glu Gly Lys Gln
           35                  40                  45

Asn Leu Val Ile Met Gly Lys Lys Thr Trp Phe Ser Ile Pro Glu Lys
 50                  55                  60

Asn Arg Pro Leu Lys Gly Arg Ile Asn Leu Val Leu Ser Arg Glu Leu
 65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
            115                 120                 125

Pro Gly His Leu Lys Leu Phe Val Thr Arg Ile Met Gln Asp Phe Glu
           130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185

<210> SEQ ID NO 4
<211> LENGTH: 189
<212> TYPE: PRT
<213> ORGANISM: Gallus gallus

<400> SEQUENCE: 4

Val Arg Ser Leu Asn Ser Ile Val Ala Val Cys Gln Asn Met Gly Ile
 1               5                  10                  15

Gly Lys Asp Gly Asn Leu Pro Trp Pro Pro Leu Arg Asn Glu Tyr Lys
            20                  25                  30

```
Tyr Phe Gln Arg Met Thr Ser Thr Ser His Val Glu Gly Lys Gln Asn
            35                  40                  45

Ala Val Ile Met Gly Lys Lys Thr Trp Phe Ser Ile Pro Glu Lys Asn
 50                  55                  60

Arg Pro Leu Lys Asp Arg Ile Asn Ile Val Leu Ser Arg Glu Leu Lys
 65                  70                  75                  80

Glu Ala Pro Lys Gly Ala His Tyr Leu Ser Lys Ser Leu Asp Asp Ala
                 85                  90                  95

Leu Ala Leu Leu Asp Ser Pro Glu Leu Lys Ser Lys Val Asp Met Val
                100                 105                 110

Trp Ile Val Gly Gly Thr Ala Val Tyr Lys Ala Ala Met Glu Lys Pro
            115                 120                 125

Ile Asn His Arg Leu Phe Val Thr Arg Ile Leu His Glu Phe Glu Ser
130                 135                 140

Asp Thr Phe Phe Pro Glu Ile Asp Tyr Lys Asp Phe Lys Leu Leu Thr
145                 150                 155                 160

Glu Tyr Pro Gly Val Pro Ala Asp Ile Gln Glu Asp Gly Ile Gln
                165                 170                 175

Tyr Lys Phe Glu Val Tyr Gln Lys Ser Val Leu Ala Gln
            180                 185

<210> SEQ ID NO 5
<211> LENGTH: 182
<212> TYPE: PRT
<213> ORGANISM: Drosophila melanogaster

<400> SEQUENCE: 5

Met Leu Arg Phe Asn Leu Ile Val Ala Val Cys Glu Asn Phe Gly Ile
1               5                  10                  15

Gly Ile Arg Gly Asp Leu Pro Trp Arg Ile Lys Ser Glu Leu Lys Tyr
            20                  25                  30

Phe Ser Arg Thr Thr Lys Arg Thr Ser Asp Pro Thr Lys Gln Asn Ala
            35                  40                  45

Val Val Met Gly Arg Lys Thr Tyr Phe Gly Val Pro Glu Ser Lys Arg
 50                  55                  60

Pro Leu Pro Asp Arg Leu Asn Ile Val Leu Ser Thr Thr Leu Gln Glu
 65                  70                  75                  80

Ser Asp Leu Pro Lys Gly Val Leu Leu Cys Pro Asn Leu Glu Thr Ala
                 85                  90                  95

Met Lys Ile Leu Glu Glu Gln Asn Glu Val Glu Asn Ile Trp Ile Val
                100                 105                 110

Gly Gly Ser Gly Val Tyr Glu Glu Ala Met Ala Ser Pro Arg Cys His
            115                 120                 125

Arg Leu Tyr Ile Thr Lys Ile Met Gln Lys Phe Asp Cys Asp Thr Phe
130                 135                 140

Phe Pro Ala Ile Pro Asp Ser Phe Arg Glu Val Ala Pro Asp Ser Asp
145                 150                 155                 160

Met Pro Leu Gly Val Gln Glu Glu Asn Gly Ile Lys Phe Glu Tyr Lys
                165                 170                 175

Ile Leu Glu Lys His Ser
            180

<210> SEQ ID NO 6
<211> LENGTH: 163
<212> TYPE: PRT
```

<213> ORGANISM: Lactobacillus casei

<400> SEQUENCE: 6

```
Met Thr Ala Phe Leu Trp Ala Gln Asp Arg Asp Gly Leu Ile Gly Lys
1               5                   10                  15

Asp Gly His Leu Pro Trp His Leu Pro Asp Asp Leu His Tyr Phe Arg
            20                  25                  30

Ala Gln Thr Val Gly Lys Ile Met Val Val Gly Arg Arg Thr Tyr Glu
            35                  40                  45

Ser Phe Pro Lys Arg Pro Leu Pro Glu Arg Thr Asn Val Val Leu Thr
    50                  55                  60

His Gln Glu Asp Tyr Gln Ala Gln Gly Ala Val Val Val His Asp Val
65                  70                  75                  80

Ala Ala Val Phe Ala Tyr Ala Lys Gln His Pro Asp Gln Glu Leu Val
                85                  90                  95

Ile Ala Gly Gly Ala Gln Ile Phe Thr Ala Phe Lys Asp Asp Val Asp
                100                 105                 110

Thr Leu Leu Val Thr Arg Leu Ala Gly Ser Phe Glu Gly Asp Thr Lys
            115                 120                 125

Met Ile Pro Leu Asn Trp Asp Asp Phe Thr Lys Val Ser Ser Arg Thr
        130                 135                 140

Val Glu Asp Thr Asn Pro Ala Leu Thr His Thr Tyr Glu Val Trp Gln
145                 150                 155                 160

Lys Lys Ala
```

SENSORS, METHODS AND KITS FOR DETECTING NADPH BASED ON RESONANCE ENERGY TRANSFER

The invention relates generally to the fields of metabolomics, molecular biology, cell biology and biosensors. More specifically, it relates to in vitro and in cellulo detection of the cofactor reduced nicotinamide adenine dinucleotide phosphate (NADPH).

Previously, the present inventors reported a principle to design semisynthetic protein-based biosensors for small molecule analytes. This principle has led to the generation of several series of biosensors, such as SNap-tag Indicator protein with a Fluorescent Intramolecular Tether (Snifit) and LUCiferase-based Indicators of Drugs (LUCIDs). See for details Brun et al., 2011; Brun, Tan, Nakata, Hinner, & Johnsson, 2009; Griss et al., 2014; Schena, Griss, & Johnsson, 2015, WO2015/007317 and WO20161/31833.

The known sensors comprise of a pair of ligand and binding protein (BP) and a pair of resonance energy transfer (RET) partners. The ligand is tethered to the BP along with the RET partners. The presence of the analyte modulates the interaction between the ligand and the BP, inducing a major conformational shift. This shift further changes the RET efficiency between the RET partners, resulting in a large change in the emission spectrum of the sensor. The ratio between the emission intensities of the two RET partners is used to quantify the analyte concentration.

To generate a functional sensor for a given analyte, the development of a suitable BP is the key prerequisite, see Griss et al. Nature Chemical Biology, 10(7), 598-603. doi: 10.1038/Nchembio.1554; WO2015/007317 and WO2016/131833 A1. Using specific ligand and BP pairs, a range of highly sensitive sensors were developed for various (clinically relevant) analytes, including topiramate (Topamax), methotrexate, trimethoprim, digoxin, digoxigenin, FK506 (tacrolimus), rapamycin, cyclosporin A, nicotinamide adenine dinucleotide (NAD) and nicotinamide adenine dinucleotide phosphate (NADP).

However, for the reduced form of nicotinamide adenine dinucleotide phosphate (NADPH), no suitable BP could previously be identified for the development of such biosensor. NADPH is a key cofactor participating ubiquitously in the redox reactions regulating the cell metabolism. NADPH provides the reducing equivalents for the biosynthetic reactions and the oxidation-reduction involved in the protection against the toxicity of reactive oxygen species (ROS), allowing the regeneration of glutathione (GSH). NADPH is also used for anabolic pathways, such as lipid synthesis, cholesterol synthesis, and fatty acid chain elongation. The NADPH system is also responsible for generating free radicals in immune cells. These radicals are used to destroy pathogens in a process termed the respiratory burst. It is the source of the reducing equivalents for the cytochrome P450 hydroxylation of aromatic compounds, steroids, alcohols, and drugs.

Furthermore, the detection of NADPH levels is often used in the so-called coupled assays where the product of one reaction is used as the substrate of another, easily detectable reaction. When an enzymatic reaction of interest does not result in a change in the absorbance of light, a spectrophotometric assay can still be suitable for this enzyme by using the coupled assay. For example, the enzyme hexokinase can be assayed by coupling its production of glucose-6-phosphate to the production of NADPH using glucose-6-phosphate dehydrogenase.

Recognizing the need for a sensor to quantify NADPH levels in (clinical) samples, the present inventors set out to identify a ligand/BP pair for NADPH and provide a RET-based sensor based thereon. The strategy chosen by the inventors was to identify a BP in which the binding of a synthetic ligand is dependent on the co-binding of NADPH and then apply the SNIFT and LUCID principle to generate a sensor. Dihydrofolate reductase (DHFR; EC 1.5.1.3) is a protein that binds to NADPH and for which numerous synthetic drugs have been identified. However, when fusing a protein domain that serves as a RET partner to the termini of E. coli DHFR or to the termini of circular permutated E. coli DHFR, the binding of the tethered ligands, as measured by the changes in the RET efficiency, did not show significant NADPH-dependency.

The inventors therefore designed a strategy in which the binding of the synthetic ligand to E. coli DHFR is weakened through the insertion of a protein domain in a loop near the binding site, such that the binding of NADPH triggers the binding of a tethered ligand. They recognized a loop in the structure of E. coli DHFR in the region between the amino acid residues 20 and 27. The loop is situated on the protein surface between a NADPH binding region (13V to 19A) and a ligand binding site (27D). The loop also contains a very flexible region (23N24L) according to the b-factor calculation. The inventors speculated that the insertion of a heterologous protein in this loop may alter the NADPH-dependency of the affinity between E. coli DHFR and its ligands.

It was found that the insertion of a protein domain into this loop can result in an NADPH-induced binding between the resulting BP and its ligand. More specifically, it was found that the NADPH-dependent affinity of the ligand is such that in a tethered form there is no significant intramolecular binding, whereas in the presence of NADPH the tethered ligand is predominantly DHFR bound. This finding allowed the development of a RET-based sensor for NADPH. Importantly, if the protein domain was simply fused to one of the two termini of E. coli DHFR and if the affinity of E. coli DHFR towards a ligand was simply weakened by point mutations, only a very moderate cofactor-dependency of the ligand binding was observed. The novel sensor for NADPH was found to be advantageous for developing quantitative, easy-to-use and scalable point-of-care test papers for complex bodily fluids such as serum and blood. For example, a BRET-based NADPH sensor enables the quantification of important metabolites such as phenylalanine through enzymatic assays.

Accordingly, the invention relates to a sensor molecule for the resonance energy transfer (RET)-based detection of the reduced nicotinamide adenine dinucleotide phosphate (NADPH), the sensor comprising a segment A connected via a linker to a segment B, wherein each of segment A and segment B comprises a member of a RET pair comprising a donor moiety and an acceptor moiety, further characterized in that (i) segment A comprises a binding protein (BP) having an NADPH-dependent affinity for its ligand, the BP being dihydrofolate reductase (DHFR; EC 1.5.1.3) or a functional homolog, fragment, derivative or variant thereof, showing the desired NADPH binding properties, and wherein the BP comprises a heterologous protein domain inserted at or replacing at least part of the region corresponding to positions 20 to 27 of E. coli DHFR, said heterologous protein domain comprising the member of the RET pair; and (ii) segment B comprises a ligand (L) capable of intramolecular binding to said BP in the presence of NADPH; such that the donor moiety and the acceptor moiety are in a suitable juxtaposition to yield a RET signal when L is bound to BP, and wherein the NADPH-induced binding of L to BP results in an increase in RET efficiency.

A sensor disclosed in the present invention is not taught or suggested in the art. WO2015/007317 and WO2016/131833 in the name of the applicant relate to BRET-based sensors comprising a proteinaceous moiety tethered to a synthetic ligand. WO2015/007317 discloses a methotrexate sensor based on a (circular permuted) DHFR as binding protein, TMP as intramolecular inhibitor, and NanoLuciferase and Cy3 as BRET-pair, in which the disclosed binding protein does not provide the NADPH-dependent affinity described in the present invention. WO2016/131833 discloses an NAD$^+$-sensor based on a mutant sepiapterin reductase as binding protein, and a luciferase and Cy3 as BRET pair. In order to decrease unspecific interactions of NanoLuc with other molecules, an extra protein domain like circular permuted DHFR is attached to the C-terminus of NanoLuc. Whereas the prior art teaches attaching the contiguous amino acid sequence of primary or circular permuted DHFR to luciferase, in a sensor of the present invention the DHFR sequence is always interrupted by an inserted heterologous protein domain to make its ligand affinity highly dependent on NADPH. Thus, the sensors of WO2015/007317 and WO2016/131833 are structurally and functionally distinct from a NADPH-sensor of the present invention.

In one embodiment of the present invention, a sensor molecule comprises a Fluorescence Resonance Energy Transfer (FRET) pair allowing for the FRET-mediated detection of NADPH. FRET is a distance-dependent interaction between the electronic excited states of two dye molecules in which the excitation is transferred from a donor molecule to an acceptor molecule without the emission of a photon. The efficiency of FRET is dependent on the inverse sixth power of the intermolecular separation, making it useful to monitor an analyte-induced conformational change in a sensor molecule of the invention. In most applications, FRET can be detected by the appearance of the sensitized fluorescence of the acceptor and by the quenching of the donor fluorescence. Primary conditions for FRET are that the donor and acceptor molecules must be in close proximity (typically 10-100 Å) and that the absorption spectrum of the acceptor must overlap with the fluorescence emission spectrum of the donor. In addition, donor and acceptor transition dipole orientations must be approximately parallel. Suitable FRET donor/acceptor pairs for use in a sensor of the invention are known in the art. For example, the FRET pair is selected from (i) a fluorescent protein and a self-labelling tag (e.g. SNAP-tag, CLIP-tag or Halo-tag) tethered with a synthetic molecule containing a fluorophore; (ii) two orthogonal self-labelling tags, one to attach the synthetic molecule containing a donor moiety, the other to attach an acceptor moiety fluorophore (for example SPR-Halo-p30-SNAP or SNAP-p30-CLIP-SPR); or (iii) two fluorescent proteins.

In a specific aspect, a FRET donor or acceptor is comprised within the heterologous protein domain that is inserted in the dihydrofolate reductase (DHFR; EC 1.5.1.3) or a functional homolog, fragment, derivative or variant thereof. For example, the heterologous protein domain can be a fluorescent protein, a self-labelling protein tag conjugated to a fluorophore, or a protein domain comprising an unnatural amino acid conjugated to a fluorophore.

In one aspect, the invention provides a FRET-based NADPH sensor wherein the BP comprises DHFR or a functional homolog, fragment, derivative or variant thereof wherein a self-labelling protein (SLP) tag, such as a SNAP-tag or Halo-tag, conjugated to a fluorophore is inserted in the DHFR sequence. See FIG. 1A for a schematic representation of the NADPH sensing mechanism provided by a FRET-based sensor of the invention. Preferably, the inserted SLP is a circular permutated SNAP-tag (cpSNAP) or a circular permutated Halo-tag (cpHalo). In one specific aspect, cpSNAP is obtained by creating new N- and C-termini at 91Q and 93S and by linking the original N- and C-termini by a linker of between about 10-20 amino acids. In another embodiment, the BP comprises cpHalo developed by creating new N- and C-termini at 141W and 144F and by linking the original N- and C-termini by a linker. Suitable linker sequences are known in the art. In one embodiment, the linker is a flexible Gly-rich linker, for example a flexible polypeptide linker of at least 5, preferably at least 8 Gly residues, more preferably at least 10 Gly residues. Gly has a low preference to form α-helix; thus, the lack of a side chain maximizes the freedom of the backbone conformation. Furthermore, Ser and Thr are polar residues that prefer to interact with the solvent than with the fused proteins. Thus, polypeptide linkers rich in Gly, Ser, and Thr offer special advantages: (i) rotational freedom of the polypeptide backbone, so that the adjacent domains are free to move relative to one another, (ii) enhanced solubility and (iii) resistance to proteolysis. Suitable linkers for use in the present invention comprise or consist of the sequence GGTGGSGGTGGSGGS (SEQ ID NO:1).

A limitation of FRET is the requirement for external illuminations to initiate the fluorescence transfer, which can lead to background noise in the results from direct excitation of the acceptor or to photobleaching. To avoid this drawback, a sensor of the invention is advantageously based on Bioluminescence Resonance Energy Transfer (BRET). In BRET, the donor fluorophore of the FRET pair is replaced by a bioluminescent donor protein (BDP) which, in the presence of a substrate, excites the acceptor fluorophore through the same resonance energy transfer mechanisms as FRET.

Accordingly, in one embodiment an NADPH sensor provided herein comprises a BRET pair (i.e. a BDP and an acceptor fluorophore) allowing for the BRET-mediated detection of NADPH. See FIG. 1B for a schematic representation of the NADPH sensing mechanism provided by a. BRET-based sensor of the invention. A functional sensor is formed by tethering DHFR ligand trimethoprim (TMP) and BRET acceptor fluorophore to BDP-inserted DHFR through a SNAP-tag. NADPH closes the sensor and increases the BRET efficiency between the fluorophore and BDP.

Generally, the BDP is a luciferase, for example the luciferase from *Renilla reniformis*). Alternative BDPs that can be employed in this invention are enzymes which can act directly on suitable substrates to generate a luminescent signal. Synthetic luminescent substrates for these enzymes are well known in the art and are commercially available from companies, such as Tropix Inc. (Bedford, MA, USA).

In a preferred embodiment, the BDP has luciferase activity. Luciferases, and nucleic acid constructs encoding them, are available from a variety of sources or by a variety of means. Examples of bioluminescent proteins with luciferase activity may be found in U.S. Pat. Nos. 5,229,285; 5,219,737; 5,843,746; 5,196,524; or 5,670,356. Preferred luciferases include NanoLuc™ luciferase (NLuc), *Renilla* luciferase, firefly luciferase and *Gaussia* luciferase. Also encompassed are non-naturally occurring luciferases, e.g. a mutated luciferase.

In a particular embodiment, a sensor of the invention comprises the previously described NanoLuc™ luciferase (NLuc), a 19.1 kDa, monomeric, ATP-independent enzyme that utilizes a novel substrate to produce a high intensity, glow-type luminescence. See WO 2012/061530 and Hall et al. ACS Chem Biol. 2012; 7(11):1848-57. The enzyme was generated using directed evolution from a deep-sea shrimp luciferase, creating a luciferase that is much brighter than other forms of luciferase, including both firefly (*Photinus pyralis*) and *Renilla reniformis*. The high intensity luminescence of NLuc combined with low autoluminescence of the furimazine substrate allows the sensitive detection of low levels of luciferase. Provided is therefore a sensor wherein said heterologous protein domain comprises a luciferase, preferably NLuc, and wherein segment B comprises an appropriate fluorescent acceptor, preferably Cy3 or TMR.

Very good results were obtained with a sensor wherein the heterologous protein domain comprises a circular permutated NLuc (cpNLuc). For example, cpNLuc was obtained by splitting the NLuc sequence between the residue 65E and 66G and by linking the native N- and C-termini through a linker moiety. A similar approach can be followed using a protein other than NLuc, wherein the N- and C-termini are in close proximity of each other. Suitable linkers include one, preferably two, motif(s) of the sequence GGTGGS (SEQ ID NO:1, residues 1-6). See FIG. 2A for a schematic representation of cpNLuc and its insertion in *E. coli* DHFR, thus resulting in a BP with ligand affinity highly dependent on NADPH.

As described herein above, a sensor molecule according to the invention is characterized among others by the presence of a proteinaceous segment A comprising dihydrofolate reductase (DHFR; EC 1.5.1.3) or a functional homolog, fragment, derivative or variant thereof, showing the desired NADPH binding properties.

The terms "functional fragment", "derivative" and "analog" mean proteins that retain substantially the same biological function or activity of the native DHFR protein in the invention. Functional fragments, derivatives or analogs of DHFR in the invention may be (i) proteins with one or more conservative or non-conservative amino acid substitution (preferably conservative), where the substituted amino acid residues may or may not be one encoded by the genetic code, or (ii) proteins containing substitutions of one or more amino acid residues having a substituent group, or (iii) proteins formed having the mature protein fused with another compound (such as compounds that extend the half-life of the protein, for example, polyethylene glycol), or (iv) proteins formed by having said protein fused with additional amino acid sequences (such as leader sequence or secretory sequence, or sequence used for purification of the protein or proprotein sequence, or fusion protein). In accordance with the teachings provided herein, these functional fragments, derivatives and analogs are well known to a person skilled in the art.

Hence, when referring to a DHFR polypeptide or protein, this includes variants of the polypeptide or protein with the same function but differing in the amino acid sequence. These variants include sequences obtained by deleting, inserting and/or substituting one or more (typically 1-15, preferably 1-10, more preferably 1-5, and most preferably 1-3) amino acid(s) in the sequence of the polypeptide or protein, and by adding one or more (usually less than 20, preferably less than 10, and more preferably within 5) amino acid(s) to its C-terminus and/or N-terminus. For example, in the art, substitution with amino acids of comparable or similar properties usually does not change the function of the polypeptide or protein. Amino acids with similar properties usually refer to a family of amino acids having similar side chains and have been clearly defined in the art. These families include amino acids with basic side chains (e.g., lysine, arginine, histidine), amino acids with acidic side chains (e.g., aspartate, glutamate), amino acids with uncharged polar side chain (e.g., asparagine, glutamine, serine, threonine, tyrosine, cysteine), amino acids with non-polar side chains (e.g., alanine, valine, leucine, isoleucine, proline, phenylalanine, methionine, tryptophan), amino acids with B-branched side chains (e.g., threonine, valine, isoleucine), and amino acids with aromatic side chains (e.g., tyrosine, phenylalanine, tryptophan, histidine).

According to the invention, the DHFR amino acid sequence (or functional homolog, fragment, derivative or variant thereof) is not used "as such" but it comprises a heterologous protein domain inserted at or replacing at least part of the targeting region corresponding to positions 20 to 27 of *E. coli* DHFR (UniprotKB accession number P0ABQ4 (DYR_ECOLI)).

*E. coli* DHFR sequence (SEQ ID NO:2)

```
        10         20         30         40
MISLIAALAV DRVIGMENAM PWNLPADLAW FKRNTLNKPV 50         60         70         80
IMGRHTWESI GRPLPGRKNI ILSSQPGTDD RVTWVKSVDE 90        100        110        120
AIAACGDVPE IMVIGGGRVY EQFLPKAQKL YLTHIDAEVE 130        140        150
GDTHFPDYEP DDWESVFSEF HDADAQNSHS YCFEILERR
```

The expression "inserted at" means that the amino acid of the heterologous protein is placed (e.g. recombinantly) in between two adjacent amino acid residues of choice in the stretch of amino acids found in or corresponding to residues 20 to 27 of the *E. coli* DHFR primary sequence.

The expression "replacing at least part of" means that the amino acid of the heterologous protein is placed (e.g. recombinantly) in between two non-adjacent amino acid residues of choice in the stretch of amino acids found in or corresponding to residues 20 to 27 of the *E. coli* DHFR primary sequence, such that the amino acids in between said non-adjacent residues are deleted. In one embodiment, up to 5, preferably up to 4, more preferably up to 3 residues of the DHFR primary sequence are deleted by the replacement. In a specific aspect, only a single amino acid of the targeting region corresponding to positions 20 to 27 of *E. coli* DHFR is replaced by a heterologous protein domain.

In other words, the heterologous protein domain may be inserted in the DHFR "targeting" region, such that the original DHFR amino acid residues remain present, or the heterologous protein domain can be introduced in the targeting region while removing some or all of the DHFR amino acids in said targeting region.

The expression "region corresponding to" refers to the stretch of amino acids within a given DHFR protein that is considered homologous or equivalent (e.g. on the basis of a sequence alignment) to the "targeting region" represented by amino acids at positions 20 to 27 (MPWNLPAD) of *E. coli* DHFR. See for example FIG. 2B showing a sequence alignment of DHFR sequences from *E. coli* (SEQ ID NO:2), human (SEQ ID NO:3), chicken (SEQ ID NO:4), *drosophila* (SEQ ID NO:5) and *Lactobacillus casei* (SEQ ID NO:6). The region corresponding to the residues 20-27 of *E. coli* DHFR is highlighted. Preferred DHFR variants include polypeptides whose sequence is at least about 70%, at least about 75%, at least about 80%, at least about 85%, at least about 90%, at least about 95%, at least about 98%, at least about 99%, or 100% sequence identity with a polypeptide according to those of FIG. 2B.

A person skilled in the art will be able to design and test different BP's comprising heterologous protein domains inserted at different positions in the region corresponding to positions 20 to 27 of *E. coli* DHFR.

In one embodiment, the heterologous protein domain is inserted at, or replaces at least part of the region corresponding to positions 23 to 26 of *E. coli* DHFR. In another embodiment, the heterologous protein domain is inserted at, or replaces at least part of the region corresponding to positions 22 to 25 of *E. coli* DHFR. Preferably, the heterologous protein domain is inserted at, or replaces at least part of the region corresponding to positions 22 to 24 or 23 to 25 of *E. coli* DHFR. In a specific aspect, said heterologous protein domain is inserted between residues (corresponding to) 23N and 24L of *E. coli* DHFR.

The sensor with this design is highly sensitive and selective. With the wild-type *E. coli* DHFR inserted by cpNLuc, the sensor is able to detect NADPH with a C50 of 5.6 nM. In these experiments, the C50 is defined as the concentration of NADPH that results in a 50% change of the maximum BRET ratio change. Several mutations (R98A, R44A and H45Q) have been introduced on the DHFR inserted by cpNLuc to tune the C50 of the sensor. The resulting sensors have C50s ranging from 5.6 nM to 6.2 µM (see FIG. 3C). The sensors adopt a closed conformation almost exclusively in the presence of NADPH: the wild-type *E. coli* DHFR inserted by cpNLuc shows a more than 8000 times higher preference for NADPH than for other cofactors with similar structures such as NADP+, NADH and NAD+.

The insertion of a suitable heterologous protein domain, for example cpNLuc, in the DHFR region 20-27 (the "targeting region") is key for the sensor performance. Sensors with cpNLuc inserted in *E. coli* DHFR between the residue 23 and 24 show maximum ratio changes between 1485% and 3027% in response to NADPH. In contrast, in cases where BDP is fused to the termini of *E. coli* DHFR or of the termini of circular permutated *E. coli* DHFR or circular permutated *E. coli* DHFR with reduced affinity towards its substrate, the resulting sensor only showed no or little (87%) response to NADPH, see FIG. 3D.

Accordingly, in one embodiment, the sensor comprises the *E. coli* DHFR sequence MISLIAALAV DRVIGME-NAM PWNLPADLAW FKRNTLNKPV IMGRHTWESIG-RPLPGRKNI ILSSQPGTDD RVTWVKSVDE AIAACGDVPE IMVIGGGRVYEQFLPKAQKL YLTHI-DAEVE GDTHFPDYEP DDWESVFSEFHDADAQN-SHSYCFEILERR (SEQ ID NO:2) or a mutant thereof, preferably wherein said DHFR mutant comprises one or more of the mutations R98A, R44A and H45Q, more preferably R44A and H45Q. In a specific aspect, the sensor comprises cpNLuc inserted in DHFR comprising one or more of mutations R98A, R44A and H45Q, preferably comprising mutations R44A and H45Q.

The synthetic (i.e. non-proteinaceous) segment B of a RET-based NADPH sensor comprises a ligand (L) capable of intramolecular binding to said BP in the presence of NADPH such that the donor moiety and the acceptor moiety are in a suitable juxtaposition to yield a RET signal when L is bound to BP, and wherein the NADPH-induced L binding to BP results in an increase in RET efficiency.

Hence, the tethered ligand L is capable of intramolecular binding to the wild-type DHFR. For example, L is suitably selected from the group consisting of trimethoprim (TMP), methotrexate (MTX), aminopterin (Ampt), 2,4 diamino-N10-methyl-pteroic acid (DAMPA) and other DHFR ligands. In a preferred embodiment, L is TMP.

Segment B furthermore comprises the appropriate member of the RET-pair. The tethered fluorophore should have a good RET with its partner inserted in DHFR when the sensor is in the closed conformation. The tethered fluorophore is chosen in accordance with the role played by the inserted heterologous protein domain in DHFR. When the tethered fluorophore serves as the RET acceptor, its excitation spectra should at least partially overlap with the emission spectra of the RET donor inserted in DHFR. When serving as the RET donor, its emission spectra should at least partially overlap with the excitation spectra of the RET acceptor. The fluorescent acceptor molecule is chosen to function as the BRET pair together with the BDP i.e. to accept the bioluminescence energy from the donor in the presence of an appropriate substrate. Furthermore, the fluorescent acceptor molecule is adapted to emit light after accepting the bioluminescence. The choice depends on the luciferase emission spectrum and/or the application of the sensor molecule. Suitable fluorescent acceptors to form a BRET pair include any fluorophores whose excitation spectra at least partially overlaps with the emission spectra of the respective luciferase.

Tetherable fluorophores that can be used as the luminescence acceptors in a sensor molecule of the invention comprising luciferase include Alexa Fluor dyes, in particular Alexa Fluor 488, Alexa Fluor 594; cyanine dyes such as Cy3, Cy3.5, Cy5, Cy7 and derivatives thereof, in particular sulfonated derivatives; SYTO dyes; SYBR dyes, Bodipy dyes; fluorescent proteins such as EGFP and mCherry; Atto Dyes such as Atto647N; rhodamine dyes such as carboxytetramethylrhodamine (TMR), Texas Red, silicon rhodamine; fluorescein derivatives such as carboxyfluorescein and FITC; Oregon Green; triarylmethane dyes as malachite green; naphthalimide dyes such as *Lucifer* Yellow; xanthene dyes such as SNARF-1; acridine dyes such as acridine orange; coumarins; IRDye stains such as IRDye 700DX.

The choice of the tethered fluorophore can be Alexa Fluor dyes, rhodamine dyes and cyanine dyes etc. When the luciferase is inserted into DHFR as the RET donor, very suitable tethered fluorophores include Cy3 and TMR. Accordingly, in case of a BRET-based sensor, segment B furthermore comprises an appropriate fluorescent acceptor, preferably Cy3 or TMR.

Exemplary synthetic structures to be comprised in segment B of a BRET-based sensor of the invention are the following:

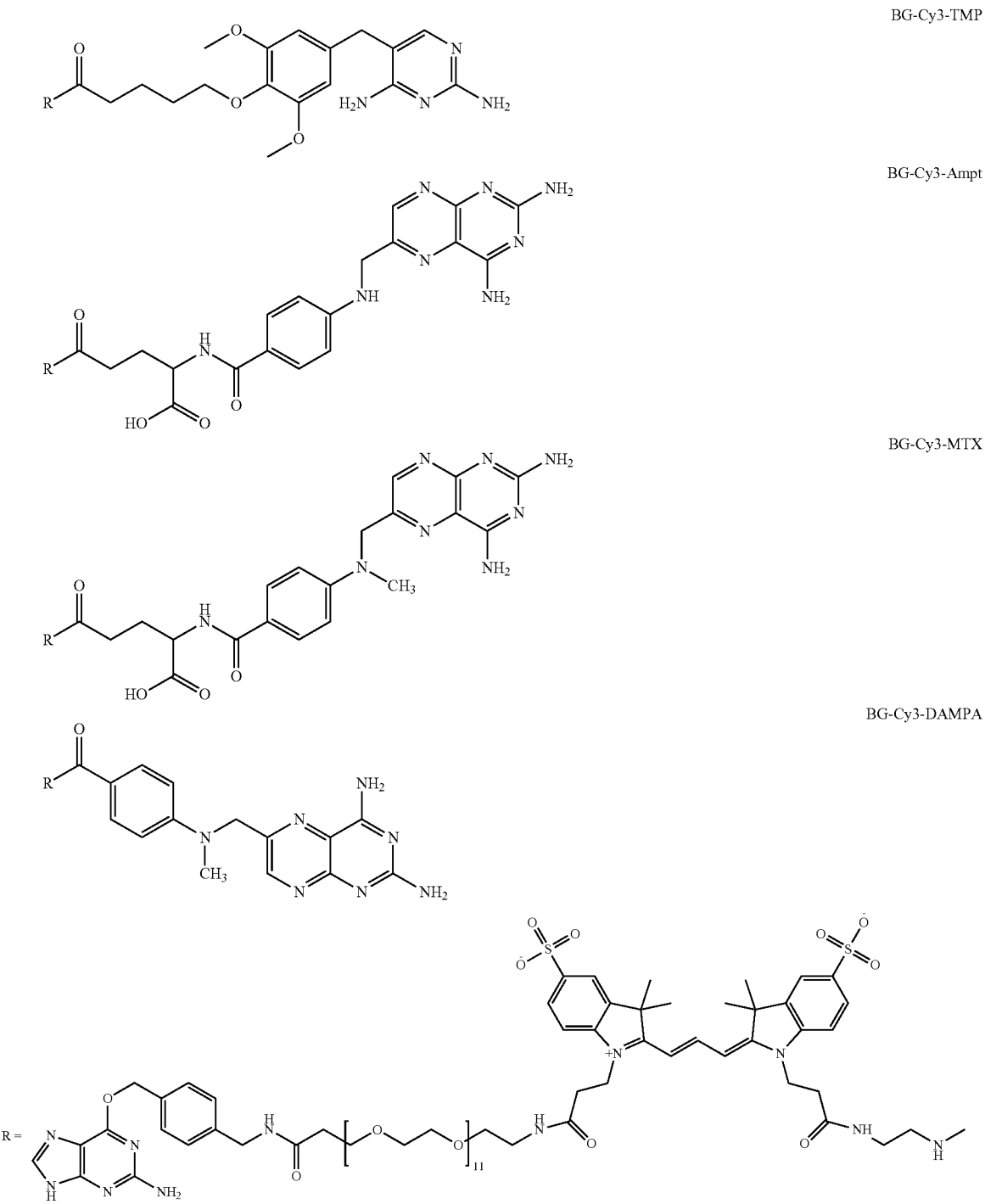

In a specific embodiment, the B segment of a sensor comprises BG-Cy3-TMP or BG-Cy3-MTX, preferably BG-Cy3-TMP.

The invention also relates to a method for providing a sensor molecule of the invention. As is illustrated in the Examples, a proteinaceous moiety representing segment A and a synthetic regulatory molecule (or precursor thereof) representing segment B are readily produced as separate entities, after which the synthetic molecule is tethered to the proteinaceous molecule using the appropriate coupling reaction, essentially as previously described for the sensor types disclosed in WO2015/007317. Hence, the method preferably comprises the steps of providing the proteinaceous moiety and the synthetic regulatory molecule or precursor thereof, and assembling both to yield the sensor molecule.

The proteinaceous moiety can be prepared using standard recombinant DNA techniques well known to those skilled in the art. For example, the BP coding sequence can be genetically introduced into the multiple cloning site of a bacterial expression vector comprising a luciferase sequence such that the BP sequence is operatively linked to the Luc coding sequence. Other proteinaceous components, like a protein labeling tag and/or linker sequences, can also be incorporated using standard techniques. The DNA constructs for various configurations of the proteinaceous moiety of a BRET sensor of the invention can be transfected/transformed in suitable cell lines (eukaryotic or prokaryotic) for its production. The various configurations of the fusion proteins produced in cells, are then purified from the transfected/transformed cells. A convenient procedure to purify a proteinaceous moiety is by affinity chromatography e.g. using a His- and/or Strep-tag engineered in the DNA construct. Standard biochemical techniques can be also used alone or in combination with affinity chromatography to purify to various levels the various fusion proteins. Finally, these purified fusion proteins can be also chemically or enzymatically modified before their tethering to the synthetic regulatory molecule. In another embodiment, the proteinaceous moiety is produced by a combination of in vivo and in vitro methods. First a fusion protein is genetically engineered and expressed in cells using recombinant techniques. The fusion protein is then purified or semi-purified before being modified by chemically or enzymatically attaching a further proteinaceous element, e.g. an element which can serve as a BP such as an antibody. The attachment of the further element can be peptide-based or chemically-based.

The synthetic regulatory molecule or precursor thereof can be synthesized by coupling the acceptor fluorophore to the intramolecular ligand, using methods known in the art. The skilled person will understand that the methods used can be selected based on the chemical nature of the fluorophore and/or the ligand. The coupling of acceptor fluorophore to the intramolecular ligand can essentially be performed according to what has been described in the art on conventional FRET-based Snifits. Also, the regulatory molecule or precursor thereof may contain an element which mediates tethering to the proteinaceous moiety. For example, if the synthetic regulatory molecule is to be site-specifically tethered to the proteinaceous moiety of the sensor molecule via a self-labelling protein such as SNAP-tag, CLIP-tag or Halo-Tag, the synthetic regulatory molecule must contain the appropriate reactive group such as a reactive group for hAGT, a O6-benzylguanine (BG), O4-benzyl-2-chloro-6-aminopyrimidine (CP) or O2-benzylcytosine (BC) derivative or a chloroalkane. Reactive groups mediating the tethering may be advantageously coupled to the fluorophore acceptor molecule via a spacer comprising several polyethylene glycol (PEG) units. For example, a spacer of 10-15 PEG units is suitably used. In a specific embodiment, the spacer is an 11-unit polyethylene glycol spacer (PEG11 linker). See for example Brun et al. J Am Chem Soc. 2009; 131(16):5873-84, and the examples herein below.

As will be appreciated by a person skilled in the art, an NADPH-sensor of the invention has broad applications and can be used in many different assay formats, be it in solution or attached to a solid support.

It was found that by absorbing a BRET-based NADPH sensor of the invention to a solid carrier such as paper or by immobilizing the BRET sensor prior to measurement to a solid carrier such as a glass surface, the interference from the absorbance of the sample at the emission wavelength of the sensor is minimized. This then allows for the analysis of complex samples, like serum. Therefore, in a specific aspect, the sensor molecule is immobilized or absorbed to a solid carrier, preferably glass, membrane (e.g. nitrocellulose), a transparent plastic, a gold surface, paper or a gel. In a preferred embodiment, it is absorbed to chromatography or filter paper. The sensor molecule may be freeze-dried after application to the solid support in order to increase its stability. Also provided is an analytical device comprising an NADPH sensor molecule according to the invention, wherein the sensor molecule is arranged in such a manner that, when the device is in use for detecting an analyte of interest in a sample, the photons that are emitted from the sensor molecule and that are collected by a detector pass through the sample for a distance shorter than 330 µm. For example, the sensor molecule is immobilized or absorbed to a solid carrier, preferably a glass or transparent plastic. In one aspect, the sensor molecule is absorbed to a paper or membrane sheet, preferably to nitrocellulose, chromatography paper or filter paper. In another aspect, the sensor molecule is comprised in a thin film, or confined in a tube, capillary or (microfluidic) chamber.

In a preferred embodiment, the invention provides a quantitative point-of-care test format for detecting NADPH, comprising a (freeze-dried) NADPH sensor of the invention absorbed to or immobilized on a paper support, like a small paper disk. As will be appreciated by the person skilled in the art, this format is highly suitable as portable, "mix-and-measure" sensors for the precise point-of-care quantification of metabolites, for example amino acids, especially for analyzing complex (biological) samples. In a preferred aspect, the analytical device is or can be hand-held, thus allowing for on-site analyte measurements. Following incubation, the BRET signal can be detected by a simple camera, even a hand-held, camera-equipped SmartPhone. Thus, also provided is a BRET sensor molecule immobilized or absorbed to a solid carrier wherein the area comprising the immobilized sensor molecule furthermore comprises a luciferase substrate.

The invention further provides a method for the fluorescence or luminescence-based in vitro detection of the concentration of NADPH in a sample, the method comprising (a) contacting the sample with a sensor molecule according to the invention under conditions allowing for an NADPH-dependent binding of said L to BP; and (b) analyzing a change in a signal generated by modulation of the spectroscopic properties of the fluorophore or emission spectra of the sensor molecule and relating the signal change to the concentration of NADPH in the sample.

The sample can be a biological sample or a fraction thereof, preferably a cell lysate or a bodily fluid, more preferably selected from the group consisting of blood, serum, saliva, urine, spinal fluid, pus, sweat, tears, breast milk. A method of the invention is advantageously used for light-absorbing samples, particularly samples that absorb in the blue light region such as a sample containing serum components. A method of the invention is also compatible with very low sample volumes, e.g. volumes of less than five microliters still provide a satisfactory assay outcome. A method for the invention is also advantageously used for the precise quantification of analytes of interest and thus can result in immediate therapeutic actions.

Typically, a sample to be analyzed in a method according to the invention comprises (i) an unknown concentration of NADPH and/or (ii) an unknown concentration of an enzyme that generates or consumes NADPH. The method can be performed in solution or in a (semi) solid phase format. Preferably, the sensor molecule is arranged in such a manner that, when in use for detecting NADPH in a sample, the photons that are emitted from the sensor molecule and that are collected by a detector pass through the sample for a distance shorter than 330 µm.

In one embodiment, the sample is contacted with the sensor while the sensor is immobilized or absorbed onto a solid carrier, preferably wherein said solid carrier is paper or a transparent object, more preferably chromatography or filter paper, a glass or transparent plastic. In another embodiment, the sample is contacted with the sensor while the sensor is in solution, e.g. using a multi-well plate.

Also provided is a kit comprising a sensor molecule according to the invention and a solid carrier, preferably wherein said solid carrier is paper or a transparent object, more preferably chromatography or filter paper, a glass or transparent plastic. In one aspect, the kit comprises a BRET-based sensor, further comprising a luciferase substrate, preferably coelenterazine, furimazine or derivative thereof.

A still further embodiment provides the use of a sensor molecule and/or kit according to the invention for the fluorescence or luminescence-based detection of NADPH.

For example, a sensor and/or kit is advantageously used in one or more of the following applications:
(i) ex vivo clinical or diagnostic testing, preferably performed in serum or bodily fluid;
(ii) ex vivo enzymatic assays that involve the formation or consumption of NADPH;
(iii) ex vivo high-throughput screening, preferably for compounds that can modulate NADPH in cells or for the validation of the toxicity profile of therapeutic drugs;
(iv) live cell measurements, preferably comprising the use of a widefield fluorescence microscope, confocal fluorescence microscope or a Fluorescence Lifetime Imaging Microscopy (FLIM) system with appropriate excitation and emission filters.

The developed sensor for NADPH can be used virtually in any enzymatic assays that follow generally the formation or consumption of NADPH. This could not only be useful for the applications in the research field (e.g. the characterization directly or indirectly of numerous enzymes activity) but also in routine clinical tests, where the activity of diverse enzymes, metabolites or other molecules are measured for diagnostic purposes. As example, the following enzyme activity assays, which measure the concentration change of NADPH by absorbance, can be performed in serum or other body fluids in clinical labs, such as glucose-6-phosphate dehydrogenase (G6PDH) assay and glutamate dehydrogenase assay. The following molecules are also routinely measured in serum or other body fluids (urine and LCR) by coupled enzymatic assays relying on the measurement of the NADPH absorbance in clinical labs: glucose (diabetes), urea (kidney disease or disorder), ammonia (liver disorder, Reye's syndrome, hepatic encephalopathy), ethanol (ethanol intoxication or poisoning).

Furthermore, the developed sensors have sufficient sensitivity, reliability and stability to be used in high-throughput screenings that would measure NADPH. Samples could generally come from cell lysates, serum or other body fluids. As example, the sensors could be used for the high-throughput screening of large libraries of compounds in order to find therapeutics that can modulate NADPH in cells. Targeting the NADPH metabolism with therapeutic drugs can be considered as a new strategy for e.g. cancer treatment. In another example, the sensors could be used in high-throughput screening for the validation of the toxicity profile of therapeutic drugs. Therapeutic drugs that alters significantly the levels of NADPH, as side-effects, may possess severe cytotoxicity.

LEGEND TO THE FIGURES

FIG. 1. (A) Pictorial description of the general sensing mechanism of a FRET-based NADPH sensor. A functional sensor is formed by tethering a DHFR ligand and a FRET donor fluorophore through a self-labeling protein tag (SLP1) to the DHFR inserted/interrupted by another orthogonal self-labeling protein (SLP2) which is labeled by a FRET acceptor. NADPH closes the sensor and increases the FRET efficiency between the FRET pair. P30 indicates a poly-L-proline linker moiety. (B) Pictorial description of the general sensing mechanism of a BRET-based NADPH sensor comprising a bioluminescent donor protein (BDP). A functional sensor is formed by tethering a DHFR ligand and a BRET acceptor fluorophore to the BDP-inserted DHFR through a SNAP-tag. NADPH closes the sensor and increases the BRET efficiency between fluorophore and BDP. P30 indicates a poly-L-proline linker moiety.

FIG. 2. (A) Schematic representation of cpNLuc (PBD ID 5BOU) and its insertion in E. coli DHFR (PDB ID 4PDJ) (B) Sequence alignment of DHFR from E. coli (P0ABQ4), human (P00374), chicken (P00378), Drosophila (P17719) and Lactobacillus casei (P00381). The highlighted areas in yellow correspond to the residues at positions 20-27 of E. coli DHFR.

FIG. 3. (A) Pictorial description of the sensing mechanism of a BRET-based NADPH sensor where BDP is cpNLuc. A functional sensor is formed by tethering a DHFR ligand TMP and a BRET acceptor Cy3 to the cpNLuc-inserted DHFR through a SNAP-tag. NADPH closes the sensor and increases the BRET efficiency between the Cy3 and cpNLuc. (B) Chemical structure of the tethered compound. Benzylguanine (BG) tethers covalently the Cy3 and TMP to the SNAP-tag. A peg11 linker is placed between the BG and Cy3. (C) Response curve of the sensor titrated with NADPH. Various mutations are introduced on the cpNLuc-inserted DHFR to tune the C50 of the sensor. The resulting variants have C50s ranging from 5.6 nM to 6.2 µM. (D) NADPH response curve of sensors generated by inserting cpNLuc into DHFR (red) and by fusing NLuc to the N-terminus of either DHFR (white), circular permutated DHFR (grey), or circular permutated DHFR with a mutation (black). (E) Fluorescent polarization assay to measure affinity between TMP and cpNLuc-inserted DHFR as BP. (F) Fluorescent polarization assay to measure affinity between TMP and wild-type DHFR as BP.

FIG. 4. (A) Quantification of glucose using NADPH BRET sensor. (B) Quantification of glutamate using NADPH BRET sensor.

FIG. 5. (A) Response curve of the test paper titrated with NADPH. The sensor emission ratios are obtained by analyzing the photo. The ratios are plotted with the corresponding NADPH concentration in each spot. (B) Quantification of phenylalanine spiked in blood. (C) Quantification of glucose spiked in serum sample. (D) Quantification of glutamate spiked in serum sample. The plot B, C and D show the analyte concentrations after the sample dilution in the reaction buffer.

FIG. 6. (A) Fluorescent polarization assay to measure affinity between TMP and cpSNAP-inserted DHFR as BP. (B) Fluorescent polarization assay to measure affinity between TMP and cpHalo-inserted DHFR as BP. (C) Pictorial description of the sensing mechanism of a FRET-based NADPH sensor where cpHalo is inserted in DHFR. (D) Emission spectra of FRET-based NADPH sensor with presence of NADPH at various concentrations. (E) Response curve of the FRET-based NADPH sensor titrated with NADPH.

EXPERIMENTAL SECTION

Example 1: NADPH Sensor Based on Bioluminescent Resonance Energy Transfer (BRET)

This example describes the development of a BRET-based sensor capable of sensing NADPH. Circular permuted NLuc (cpNLuc) is used as the heterologous protein domain inserted in E. coli DHFR. The cpNLuc also forms the BRET partner with a fluorophore Cy3. The Cy3 is tethered with a DHFR ligand trimethoprim in the synthetic part of the sensor. See FIG. 3A for a schematic representation of the NADPH sensing mechanism.

The proteinaceous moiety of the sensor comprises the cpNLuc-inserted DHFR, a poly-L-proline linker and a SNAP-tag. The fusion proteins were cloned in pET51b(+) plasmids and expressed in E. coli strain BL21. The DNA sequence of the plasmids was verified through Sanger sequencing. The fusion protein was purified from bacterial lysate using Ni-NTA and Strep-Tactin columns.

The synthetic moiety of the sensor contains an $O^6$-benzylguanine (BG) group for the SNAP-tag labeling, a peg11 linker, a fluorophore Cy3 and trimethoprim. The moiety as shown in FIG. 3B was prepared according to a previously described method (Griss et al. Nature Chemical Biology, 10(7), 598-603. doi: 10.1038/Nchembio.1554). The functional sensor was formed by labeling the synthetic moiety to the fusion protein. 8 µM synthetic moiety and 2 µM fusion protein were mixed in HEPES buffer containing 50 mM HEPES and 50 mM NaCl at pH 7.2. The mixture was incubated at room temperature for 1 h. The resulting sensor shown in FIG. 3A was used without further purification.

The sensor was titrated with NADPH to assess its response. NADPH at various concentrations were mixed with 100 µM sensor in 50 µL buffer (50 mM HEPES, 50 mM NaCl, pH 8.5) in a white microtiter plate (Greiner Bio-One). 50 µL of the same buffer containing 500-fold diluted furimazine (Nano-Glo Luciferase Assay Substrate, Promega) was subsequently added in each well. An EnVision Multilabel Reader (PerkinElmer) was used to measure the bioluminescent signal from the wells. The NLuc emission was measured at 460 nm (bandwidth 25 nm) while the Cy3 emission was measured at 595 nm (bandwidth 60 nm). To record the bioluminescent emission spectra, the same titration solutions were measured by an infinite M1000 spectrofluorometer (Tecan) with 2 nm step size, 20 nm bandwidth and 100 ms integration time.

Figure 3C:
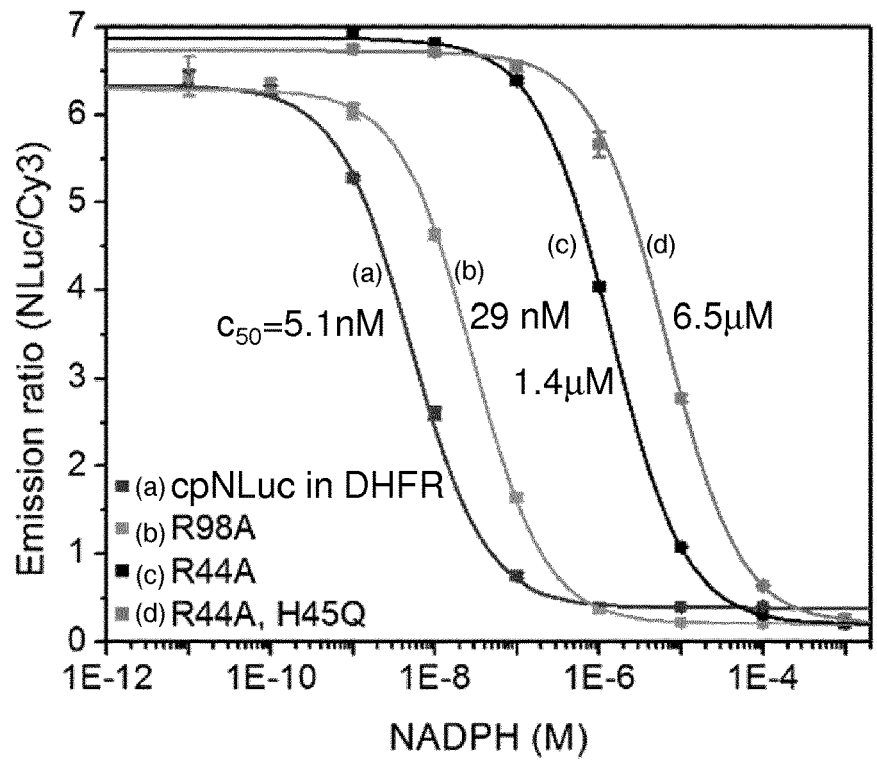

To cover a wider concentration range, several mutations (R98A, R44A and H45Q) were introduced on the DHFR inserted by cpNluc to tune the C50 of the sensor. FIG. 3C shows the response of different sensors to NADPH. The sensors demonstrated a maximum ratio change between 1485% and 3027% with C50s ranging from 5.6 nM to 6.2 µM

Example 2: Relevance of Inserting a Heterologous Protein Domain in the Targeting Region of DHFR This example compares the performance of BRET sensors generated by either the insertion of cpNLuc in between positions 23 and 24 of E. coli DHFR according to the invention, or by fusing NLuc to the N terminus of either E. coli DHFR, circular permutated E. coli DHFR (cpDHFR), or circular permutated E. coli DHFR with mutations.

Two proteinaceous moieties with NLuc that is not inserted into E. coli DHFR are designed for this comparison: SNAP-p30-NLuc-DHFR and SNAP-p30-NLuc-cpDHFR (Griss et al. Nature Chemical Biology, 10(7), 598-603. doi: 10.1038/Nchembio.1554). The fusion proteins were obtained according to the methods described in Example 1 and were further labeled with the synthetic moiety containing an O6-benzylguanine (BG) group for the SNAP-tag labeling, a peg11 linker, a fluorophore Cy3 and trimethoprim.

The labeled constructs were titrated with NADPH to assess its response according to the methods described in Example 1. However, both constructs only showed modest response (<50%) to NADPH. By contrast, the sensor with cpNLuc inserted into E. coli DHFR as BP showed a response of 1485%, see FIG. 3D.

In the absence of NADPH, the construct SNAP-p30-NLuc-cpDHFR remains in a closed conformation when TMP is used as a ligand, indicating a too strong affinity of the tethered ligand. Hence, a mutation L54G was introduced in the cpDHFR to reduce its affinity. Furthermore, a ligand with weaker affinity than TMP, namely DAMPA, was used as the tethered ligand. However, even with such improvement, the resulting construct only showed 87% change of the emission ratio in response to NADPH, see FIG. 3D.

Figure 3D:
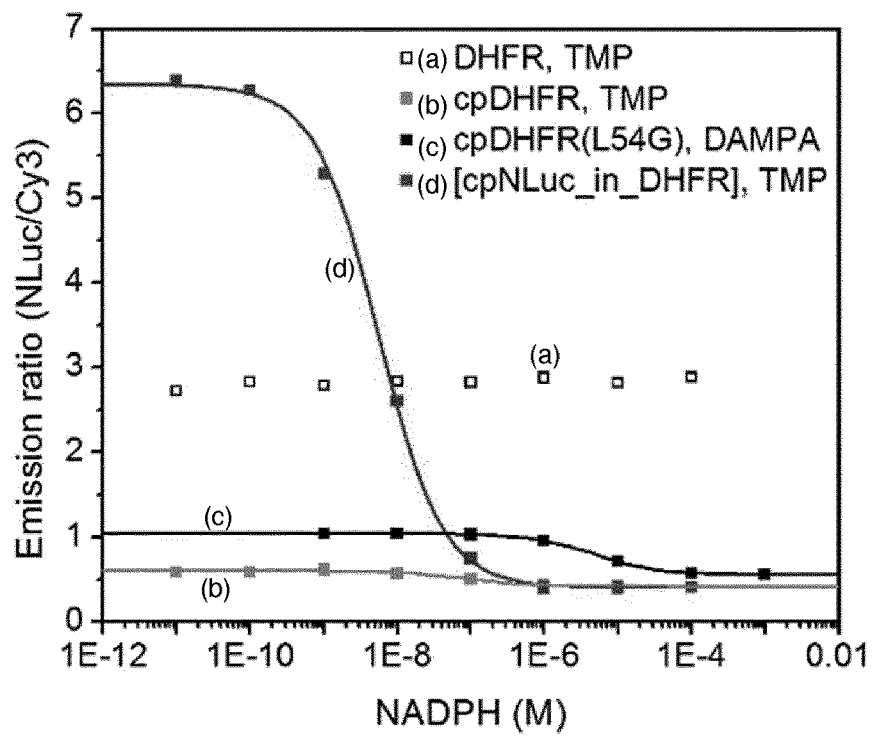

As demonstrated in Example 1 and the red plot of FIG. 3D, the insertion of cpNLuc in DHFR significantly improves the NADPH-dependent affinity of the BP towards the tethered ligand.

Figure 3E:
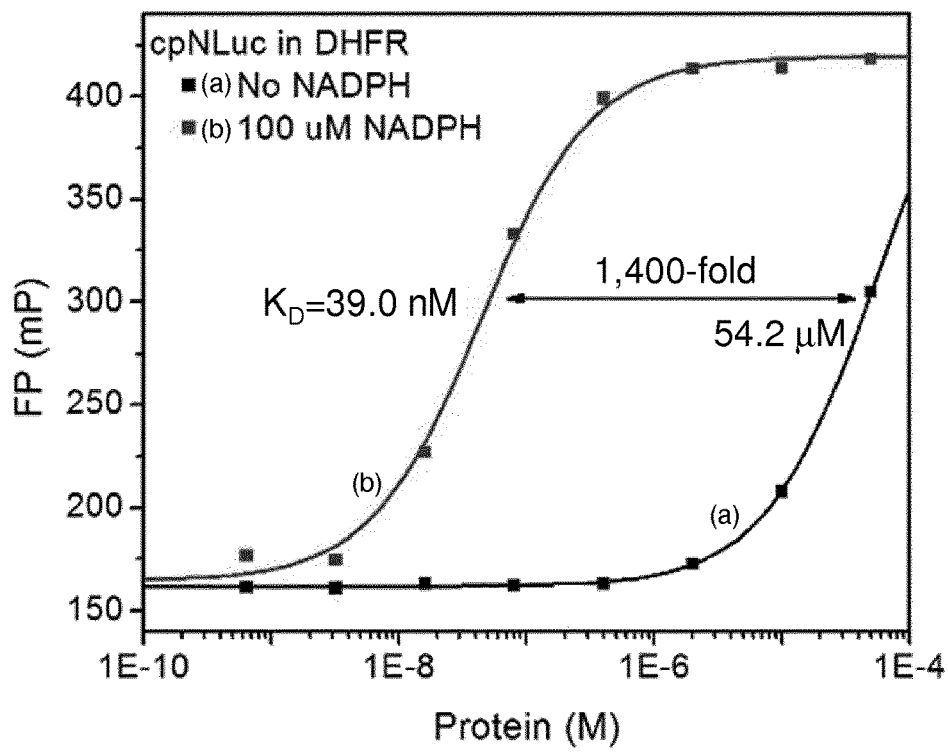
Figure 3F:
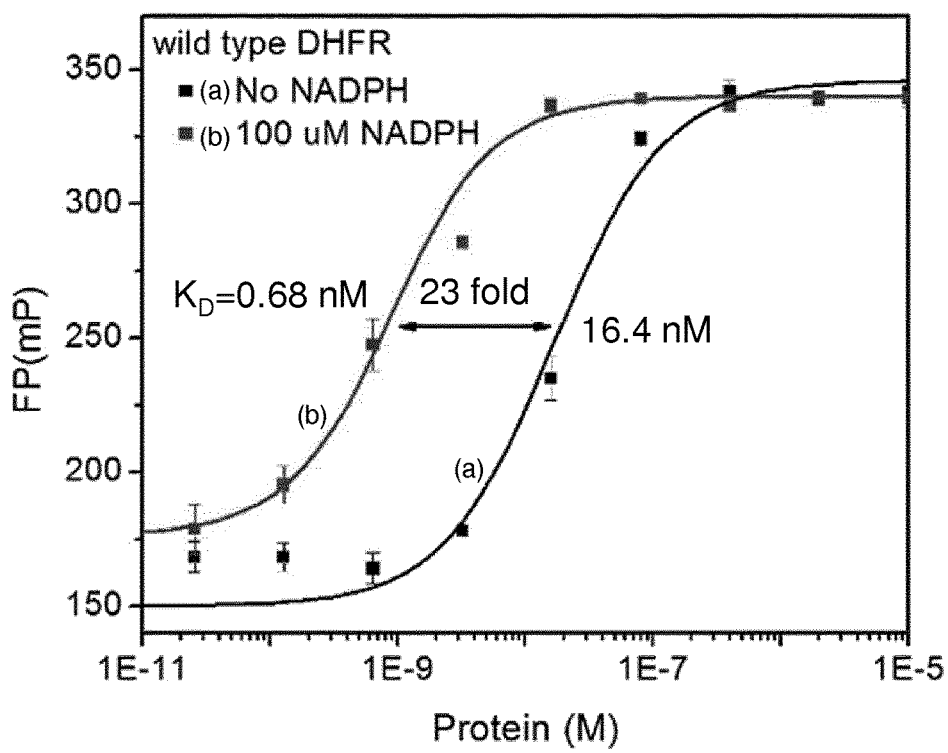

This example further demonstrates how NADPH can affect the affinity between the binding proteins and the ligand. The apparent $K_D$ between the binding proteins and the ligand was determined by fluorescent polarization assays in the absence and presence of 100 µM NADPH. In accordance with the titration results (FIG. 3D), the cpNLuc-inserted DHFR showed a 1400-fold increase of affinity towards TMP with the presence of NADPH (FIG. 3E). By contrast, NADPH only increased the affinity of the wild-type DHFR towards TMP by 23 folds (FIG. 3F).

The fluorescent polarization assays were performed by mixing various concentrations of BP with 1 nM TMP derivatized with fluorophore tetramethylrhodamine (TMP-TMR) in 100 µL of buffer (50 mM HEPES, 50 mM NaCl, pH 8.5) in a black 96-well plate (Greiner Bio-One). The fluorescent polarization values were measured using a Spark® 20M microplate reader (Tecan) with excitation wavelength at 535 nm (bandwidth 25 nm) and emission wavelength at 595 nm (bandwidth 35 nm). For receptors with an apparent $K_D$ lower than 1 nM towards TMP, 0.5 nM TMP-TMR was used in the assay.

Example 3: NADPH Sensor for Screening Enzymatic Activity in Solution

The example describes the use of an NADPH sensor to screen for a desired enzymatic activity in solution. As a proof of principle, mutants of wild-type phenylalanine dehydrogenase (PDH) were screened for NADPH-dependent enzymatic activity. The wild-type PDH takes only NADH as cofactor. A NADPH-dependent variant is needed for developing a paper-based bioluminescent assay for phenylalanine.

Wild-type PDH and 2 PDH mutants were expressed and purified in E. coli strain BL21. Ni-NTA and Strep-Tactin columns were used to purify the enzymes from the bacterial lysate. 1 µM purified enzymes were added into 50 µL buffer containing 1 nM NADPH cpNLuc-based BRET sensor (C50=1.36 µM), 1 mM $NADP^+$, 20 µM phenylalanine, 100 mM glycine, 100 mM KCl and 100 mM KOH at pH 10.4. After a 5 min incubation, 50 µL buffer containing NLuc substrate furimazine, 100 mM glycine, 100 mM KCl and 100 mM KOH at pH 10.4 was added into the previous buffer. The bioluminescent signal from the solution was measured using an EnVision Multilabel Reader (PerkinElmer). The NLuc emission was measured at 460 nm (bandwidth 25 nm) while the Cy3 emission was measured at 595 nm (bandwidth 60 nm). The intensity ratio between the NLuc and Cy3 emission was used to assess the NADPH-dependent activity of the variants. A lower NLuc/Cy3 intensity ratio indicates a higher concentration of the produced NADPH, and thus a higher desired activity.

Example 4: NADPH Sensor for Solution-Based Enzymatic Assay with Nanomolar Sensitivity The NADPH BRET sensor of Example 1 was used to develop enzymatic assays with nanomolar sensitivity. A glucose assay based on the following reaction was developed as a proof of principle:

Glucose+ATP<=>glucose-6-phosphate+ADP(Hexokinase)

G6P+NADP$^+$<=>6-phosphogluconate+NADPH+H$^+$ (G6P dehydrogenase)

20 nM to 800 nM glucose were added in a buffer containing 1 nM NADPH BRET sensor (C50=27 nM), 5 µM NADP$^+$, 250 µM ATP, 2 mM MgCl$_2$, >1 ku/L hexokinase, >1 ku/L G6P dehydrogenase, NLuc substrate furimazine, 50 mM HEPES and 50 mM NaCl at pH 8.5.

Figure 4A:
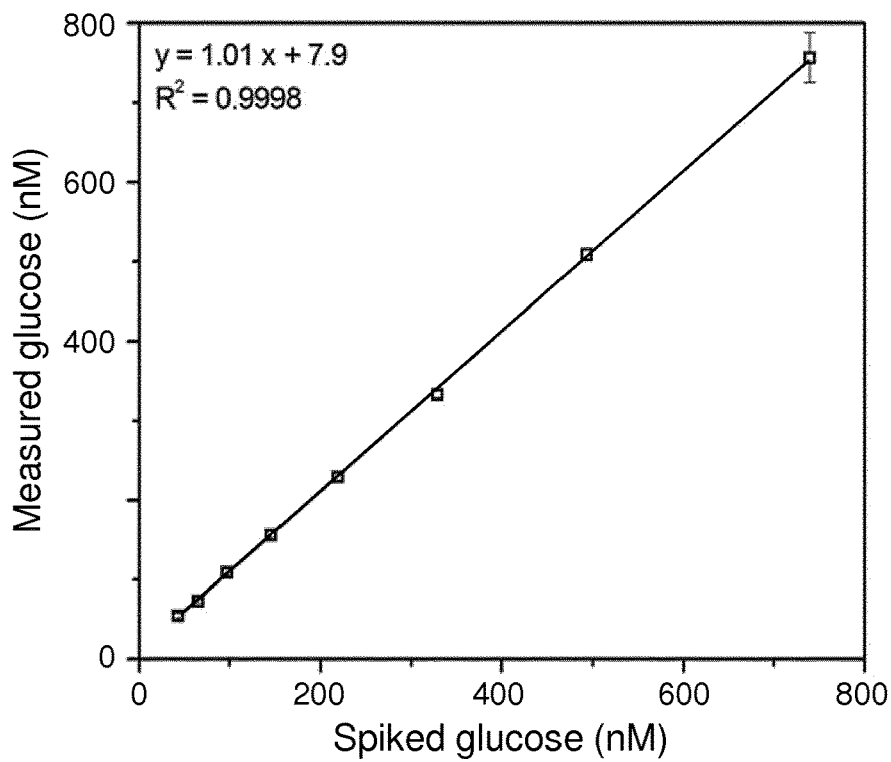
Figure 4B:
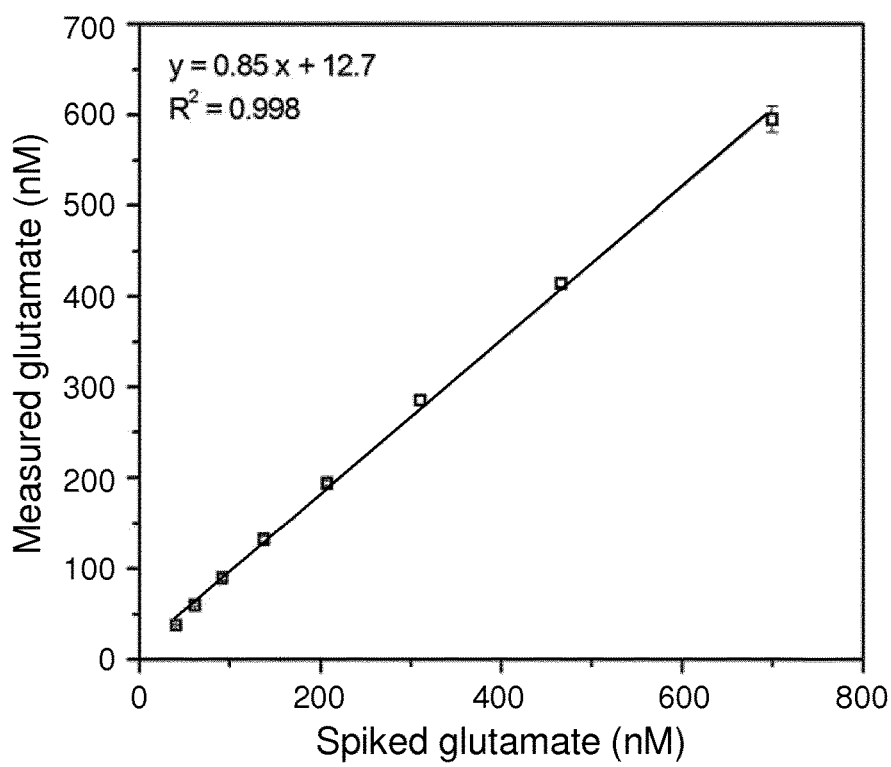

After a 5 min incubation, the bioluminescent signal from the solution was measured using an EnVision Multilabel Reader (PerkinElmer). The NLuc emission was measured at 460 nm (bandwidth 25 nm) while the Cy3 emission was measured at 595 nm (bandwidth 60 nm). The glucose concentration was obtained based on the NLuc/Cy3 emission ratio and a titration curve performed under the same condition prior to the assay (FIG. 4A).

Similarly, an enzymatic assay for glutamate was performed based on the following reaction:

Glutamate+NADP$^+$<=>ketoglutarate+NADPH (Glutamate dehydrogenase)

Samples with 20 nM to 800 nM glutamate were added in a buffer containing 1 nM NADPH BRET sensor (C50=27 nM), 10 µM NADP$^+$, 100 µM ADP, 1 mM EDTA, >1 ku/L glutamate dehydrogenase, NLuc substrate furimazine, 50 mM HEPES and 50 mM NaCl at pH 8.5.

After a 5 min incubation, the bioluminescent signal from the solution was measured and the glutamate concentration in the solution was obtained using the same procedure described above (FIG. 4B).

Example 5: Bioluminescent Test Device for Phenylalanine

The example demonstrates the use of immobilized NADPH BRET sensors to develop a quantitative point-of-care test device for the measurement of phenylalanine using a low volume of non-separated blood.

The test paper was developed based on the following enzymatic reaction:

phenylalanine+NADP$^+$<=>phenylpyruvate+NADPH (engineered phenylalanine dehydrogenase)

Test device was made by freeze-drying 0.5 pmol of NADPH sensor (C50=27 nM) on a small paper disk. The paper disk has a 6 mm diameter and the area of the disk was defined by wax-based ink serving as a hydrophobic barrier. To perform the assay, 0.5 µL of whole blood was incubated for 5 min in 24.5 µL buffer containing 2 µM engineered NADP$^+$-dependent phenylalanine dehydrogenase (see Example 3), 1 mM NADP$^+$, NLuc substrate furimazine, 100 mM glycine, 100 mM KCl and 100 mM KOH at pH 10.4. The engineered dehydrogenase consumes phenylalanine and produces NADPH stoichiometrically, which was further quantified by the test paper.

To measure the produced NADPH, 5 µL of the mixture was added onto the paper disk. The light produced by the sensor was measured using a digital camera mounted on a homemade cardboard box. The photo of the test paper was analyzed by a software that calculates the intensity ratio of the blue (NLuc) and red (Cy3) light emitted from each spot (Nature Chemical Biology, 10(7), 598-603). Phenylalanine concentrations in each spot were further calculated based on the emission ratios and a titration curve obtained under the same condition (FIGS. 5 A and B).

Example 6: Bioluminescent Test Device for Glucose

The NADPH BRET sensor was employed to develop a quantitative point-of-care test paper for glucose. The test paper was developed based on the following enzymatic reaction:

Glucose+ATP<=>glucose-6-phosphate+ADP (Hexokinase)

G6P+NADP<=>6-phosphogluconate+NADPH+H$^+$ (G6P dehydrogenase)

The test paper was made by freeze-drying 0.5 pmol of immobilized NADPH sensor (C50=1.36 µM) on a small paper disk. 0.5 µL of sample was diluted 500 folds in a buffer containing 100 µM NADP$^+$, 1 mM ATP, 2 mM MgCl$_2$, >1 ku/L hexokinase, >1 ku/L G6P dehydrogenase, NLuc substrate furimazine, 50 mM HEPES and 50 mM NaCl at pH 8.5.

Figure 5A:
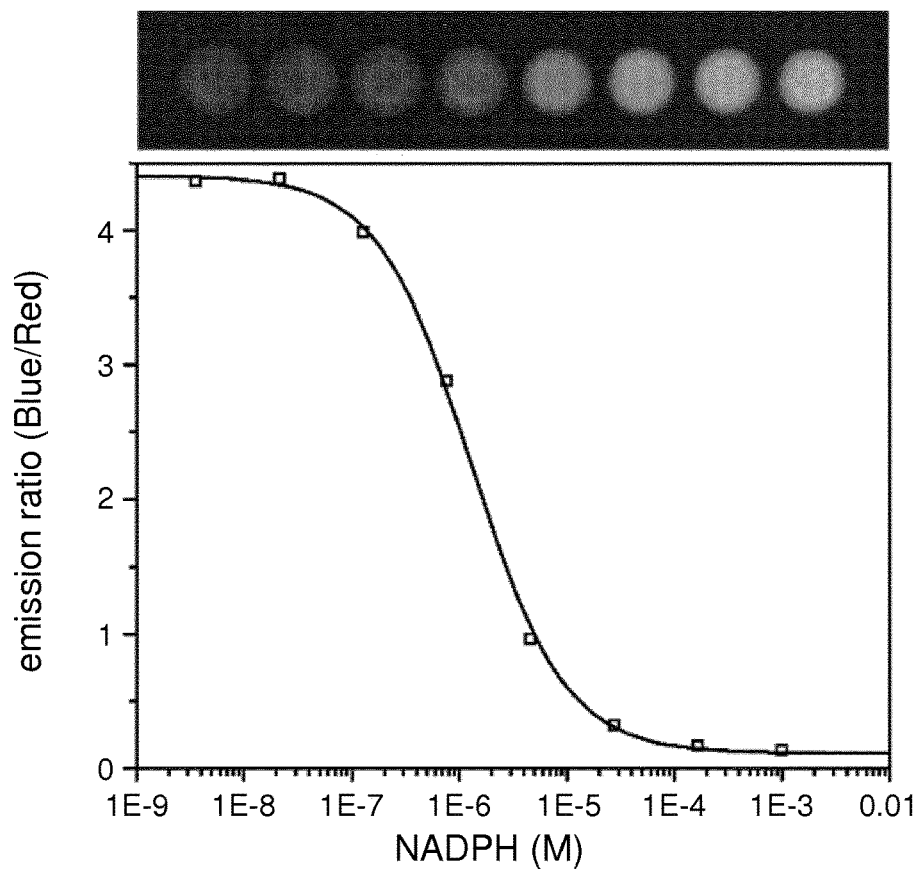
Figure 5B:
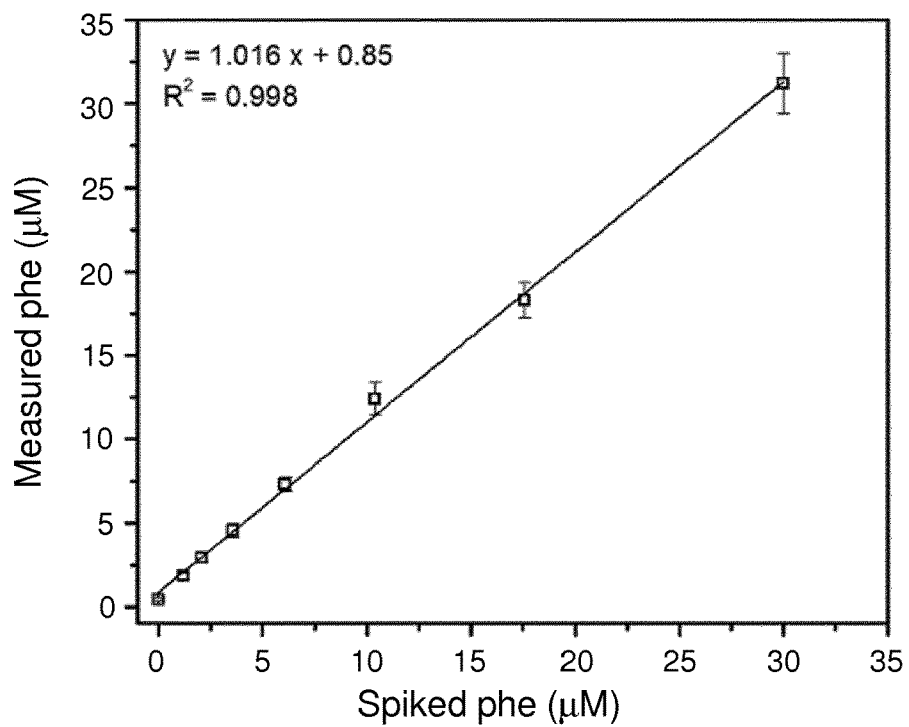
Figure 5C:
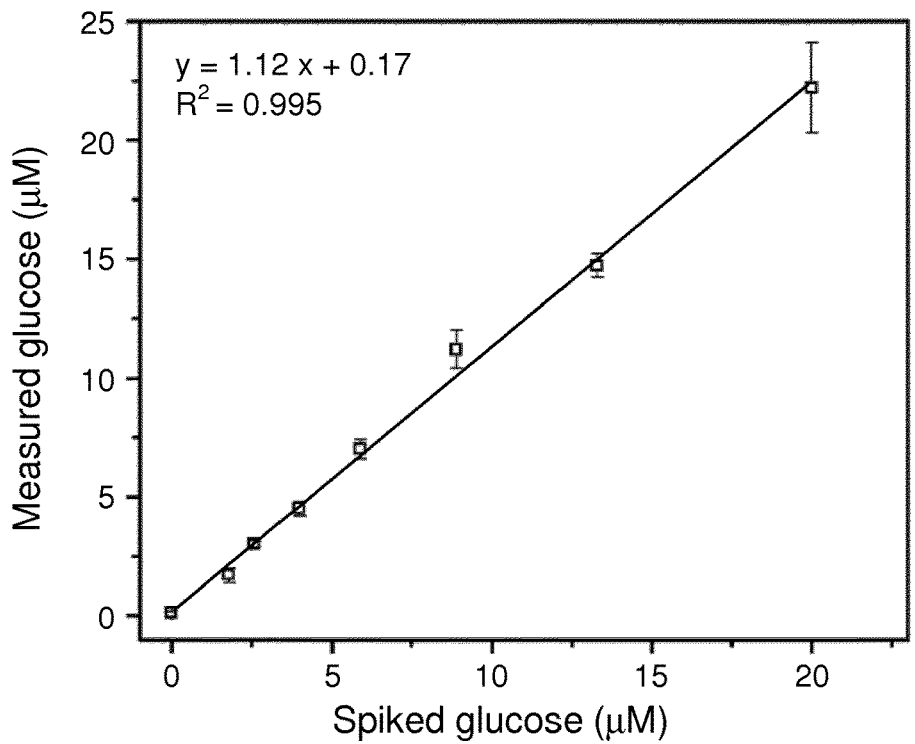

After a 5 min incubation, glucose concentration in the sample was quantified by measuring the stoichiometrically produced NADPH using the test paper and camera (FIG. 5C).

Example 7: Bioluminescent Test Device for Glutamate

The example shows the use of NADPH BRET sensor to develop a quantitative point-of-care test paper for glutamate. The assay was developed based on the following enzymatic reaction:

glutamate+NADP$^+$<=>ketoglutarate+NADPH (Glutamate dehydrogenase)

The test paper was made by freeze-drying 0.5 pmol of NADPH sensor (C50=1.36 µM) on a small paper disk. 0.5 µL of sample was diluted 500 folds in a buffer containing 100 µM NADP$^+$, 1 mM ADP, >1 ku/L glutamate dehydrogenase, NLuc substrate furimazine, 50 mM HEPES and 50 mM NaCl at pH 8.5.

Figure 5D:
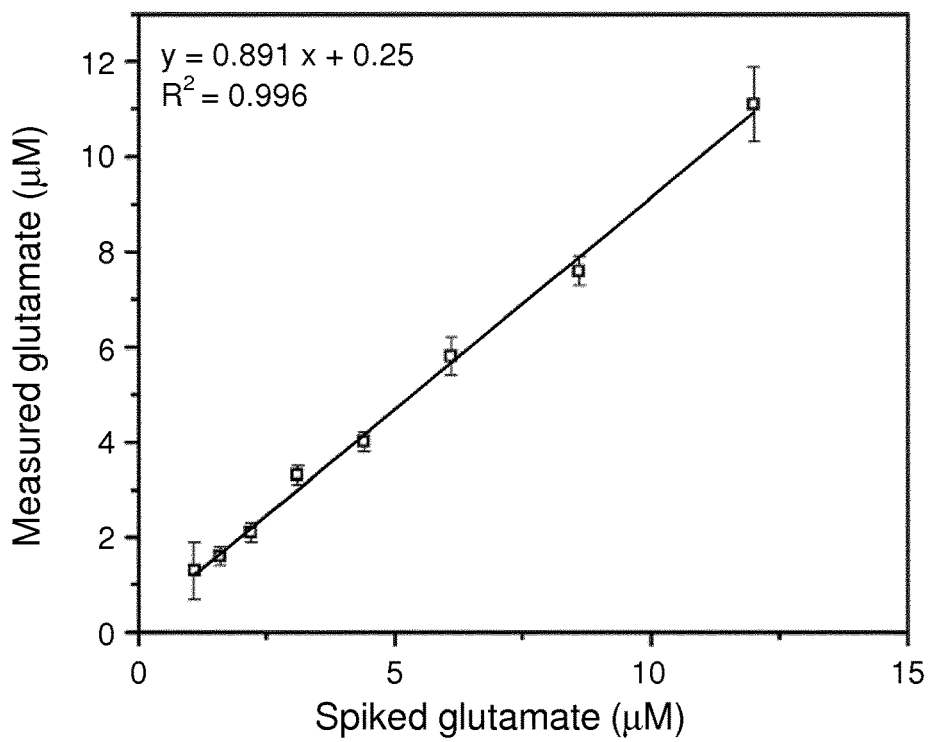

After a 5 min incubation, glutamate concentration in the sample was quantified by measuring the stoichiometrically produced NADPH using the test paper and camera (FIG. 5D).

Example 8: FRET-Based NADPH Sensors

Example 1 described a BRET-based sensor for NADPH with the BP developed by inserting a circular permuted Nanoluc (cpNLuc) as the heterologous protein domain in DHFR. The affinity of this BP towards the ligand TMP demonstrates a dramatically improved NADPH-dependency compared to the wild-type DHFR (FIGS. 3E&F). The presence of NADPH decreased the $K_D$ between the BP and TMP from 54 µM to 39 nM, representing a 1,400-fold increase of affinity, while the wild-type DHFR only demonstrate a 23-fold increase of affinity towards TMP when NADPH is present.

The present example demonstrates that similar advantageous results are achieved when other heterologous protein domains are inserted in the sequence of DHFR. Circular permutated SNAP-tag (cpSNAP) or Halo-tag (cpHalo) were inserted between the amino acid residue 23N and 24L of DHFR to afford BPs with strong NADPH-dependent affinity towards the ligand TMP. The BP with cpHalo was further used to afford a FRET-based sensor for NADPH.

The cpSNAP was developed by creating new N- and C-termini at 91Q and 93S and by linking the original N- and C-termini by a GGTGGSGGTGGSGGS linker (SEQ ID NO:1). The cpHalo was developed by creating new N- and C-termini at 141W and 144F and by linking the original N- and C-termini by a GGTGGSGGTGGSGGS linker (SEQ ID NO:1). The fusion proteins were produced as described in Example 1.

Figure 6A:
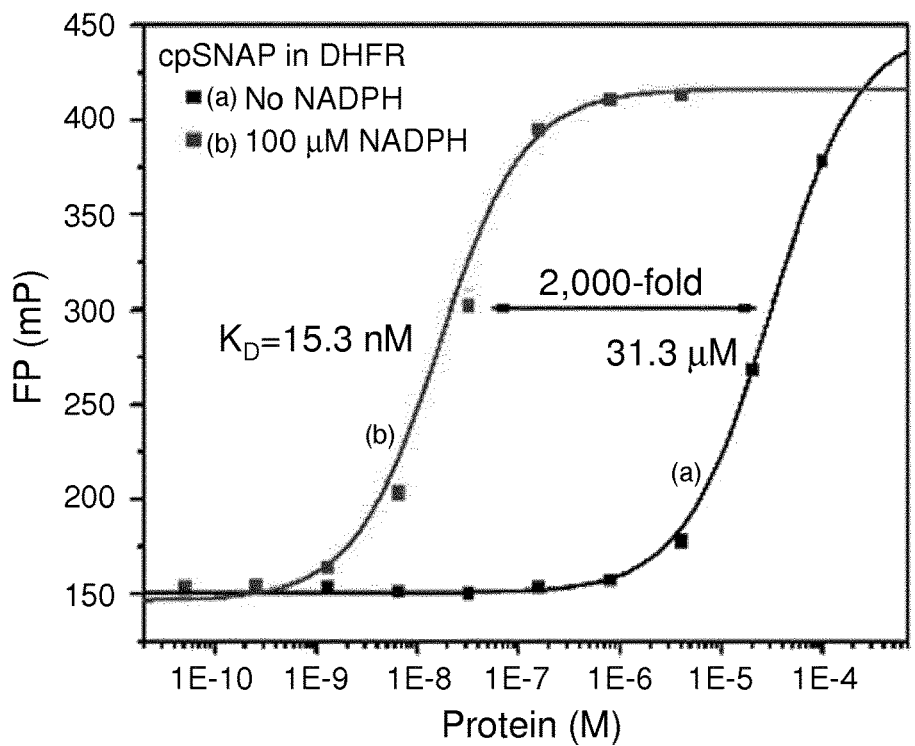
Figure 6B:
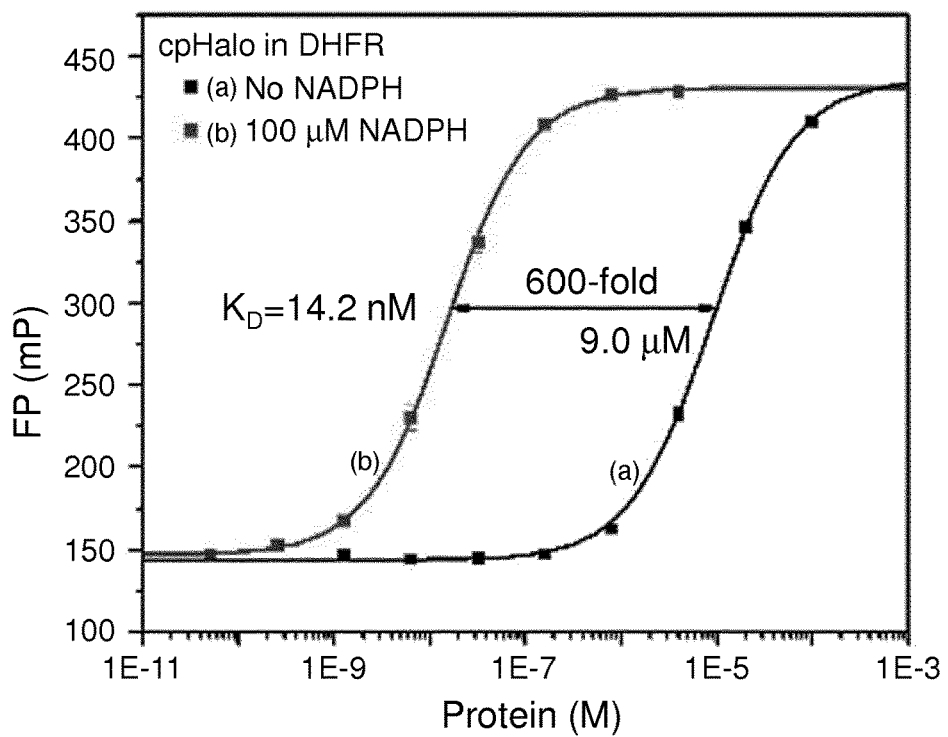
Figure 6C:
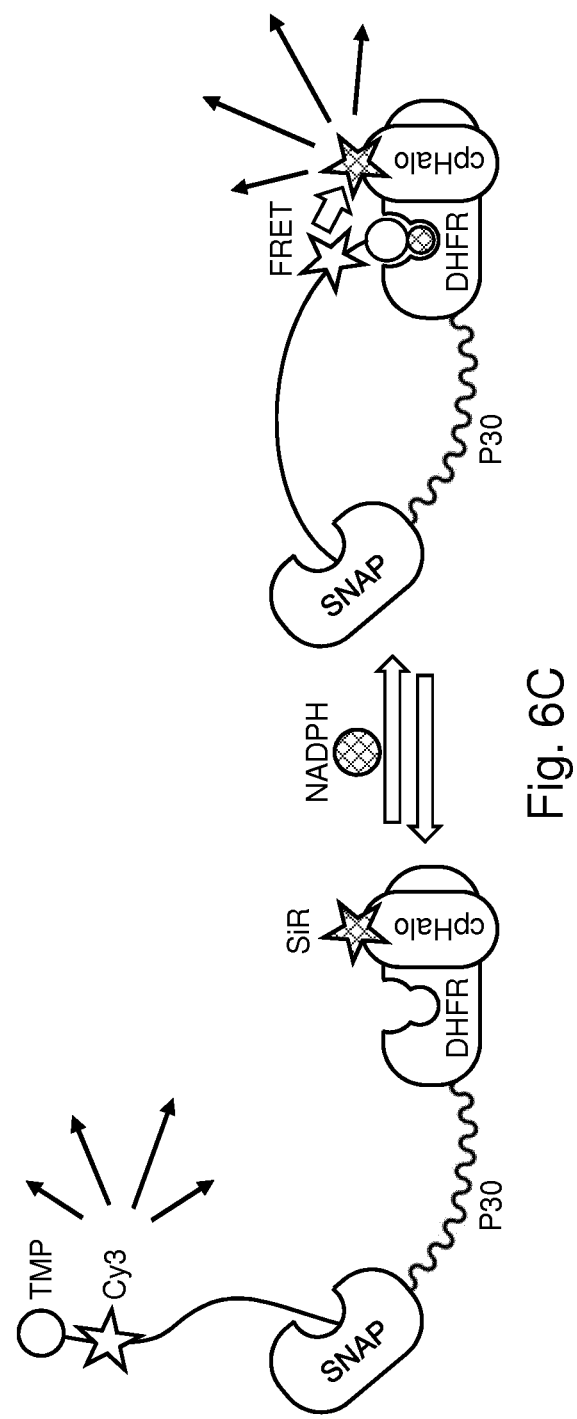
Figure 6D:
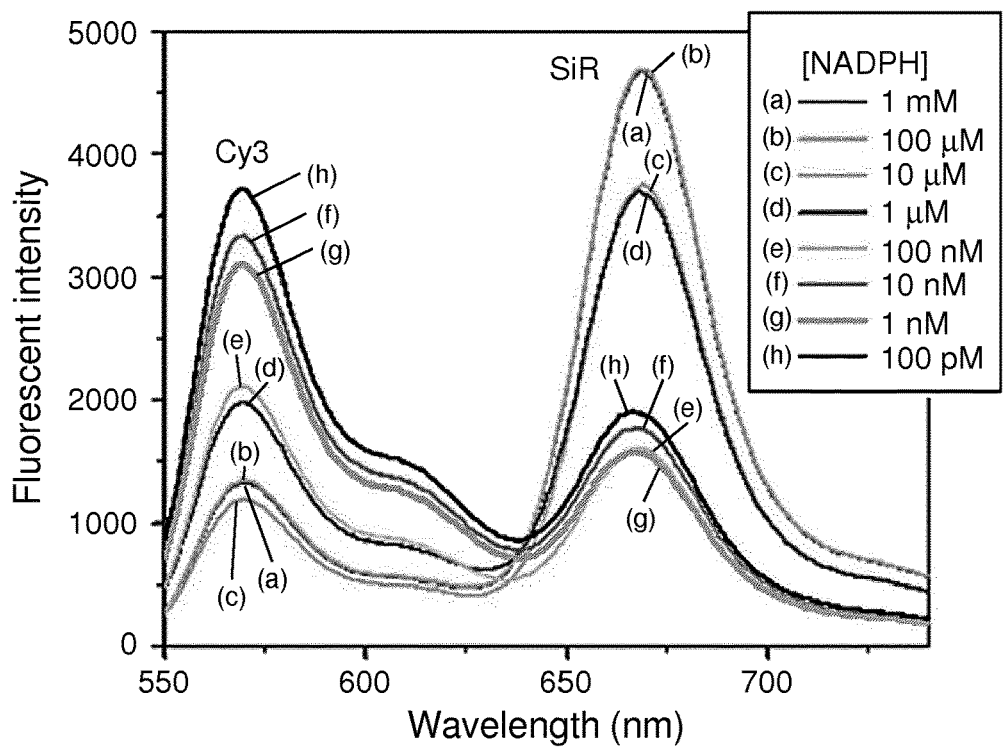

The BPs developed by inserting either one of the heterologous protein domains (cpSNAP or cpHalo) showed a dramatically improved NADPH-dependent affinity towards the ligand. This affinity was measured by $K_D$ through fluorescent polarization assays as described in Example 2. By inserting cpSNAP, NADPH increased 2,000-fold the affinity between the BP and TMP (FIG. 6A). Similarly, by inserting cpHalo, NADPH increased 600-fold the affinity between the BP and TMP (FIG. 6B).

A FRET-based sensor for NADPH was developed by fusing the BP comprising the inserted cpHalo to a poly-L-proline linker and a SNAP-tag. The cpHalo was labeled with a fluorophore Halo-SiR (Lukinavicius et al., 2013. Nat Chem, 5(2), 132-139) and the SNAP-tag was labeled with the synthetic molecule containing an $O^6$-benzylguanine (BG) group for SNAP-tag labeling, a peg11 linker, a fluorophore Cy3 and TMP. The tethered fluorophore Cy3 is known to be a good FRET pair of Halo-SiR. See FIG. 6B for a schematic representation of the NADPH sensing mechanism.

The functional sensor was formed by labeling Halo-SiR and the synthetic molecule to the fusion protein. 8 µM Halo-SiR and 8 µM synthetic molecule were mixed with 2 µM fusion protein in HEPES buffer containing 50 mM HEPES and 50 mM NaCl at pH 7.2. The mixture was incubated at room temperature for 1 h. The labeled protein was then washed three times by HEPES buffer containing 50 mM HEPES and 50 mM NaCl at pH 7.2 using a protein centrifugal filter (Amicon Ultra) with a cut-off of 50 KDa.

The sensor was titrated with NADPH to assess its response. NADPH at various concentrations were mixed with 10 nM sensor in 100 µL buffer (50 mM HEPES, 50 mM NaCl, pH 8.5) in a black microtiter plate (Greiner Bio-One). A Spark® 20M microplate reader (Tecan) was used to record the emission spectra (FIG. 6D) of the sensor from 550 nm to 740 nm with excitation at 520 nm, 1 nm step size, 10 nm bandwidth and 40 µs integration time.

Figure 6E:
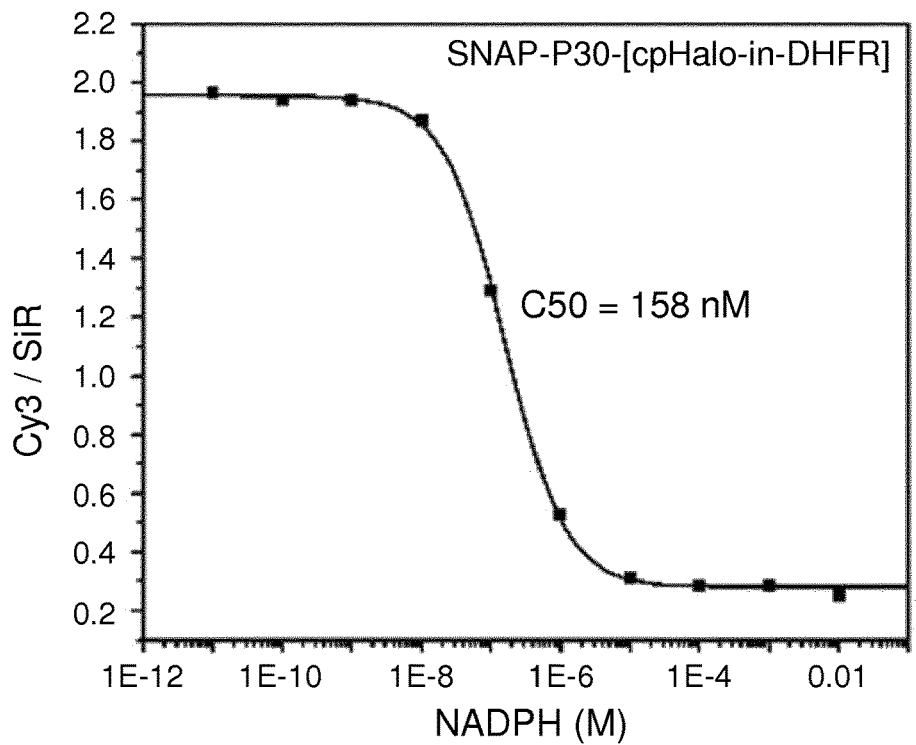

FIG. 6E shows the sensor's response to NADPH. The sensor demonstrated a maximum ratio change of 700% and a C50 of 158 nM.

REFERENCES

Brun, M. A. et al. (2011). Journal of the American Chemical Society, 133(40), 16235-16242. doi: 10.1021/ja206915m Brun, M. A. et al. (2009). Journal of the American Chemical Society, 131(16), 5873-5884. doi: 10.1021/ja900149e Griss, R. et al., (2014). Nature Chemical Biology, 10(7), 598-603. doi: 10.1038/Nchembio.1554

Schena, A. et al., (2015). Nature Communications, 6. doi: Artn 7830 10.1038/Ncomms8830

Xue, L. et al., (2016). Journal of the American Chemical Society, 138(16), 5258-5261. doi: 10.1021/jacs.6b03034

The invention claimed is:

1. A sensor molecule for the bioluminescence resonance energy transfer (BRET)-based detection of reduced nicotinamide adenine dinucleotide phosphate (NADPH), the sensor comprising a segment A connected via a linker to a segment B, wherein each of segment A and segment B comprises a member of a BRET pair comprising a donor moiety and an acceptor moiety, further characterized in that (i) segment A comprises a binding protein (BP) for NADPH, the BP being dihydrofolate reductase (DHFR; EC 1.5.1.3) of *E. coli* (UniprotKB accession number P0ABQ4) having the amino acid sequence of SEQ ID NO:2 or a variant thereof having at least 95% sequence identity to SEQ ID NO:2, or a functional homolog thereof selected from SEQ ID NOS:3-6 and variants thereof having at least 95% sequence identity to any of SEQ ID NOS:3-6, wherein the BP is capable of binding NADPH, and wherein the BP comprises a heterologous protein domain inserted at or replacing at least part of the region corresponding to positions 22 to 25 of *E. coli* DHFR, said heterologous protein domain comprising as one member of the BRET pair a luciferase enzyme as bioluminescent donor protein (BDP);

(ii) segment B comprises a ligand (L) capable of intramolecular binding to said BP only in the presence of NADPH and wherein segment B comprises a fluorescence acceptor moiety whose excitation spectrum at least partially overlaps with an emission spectrum of the luciferase;

wherein the donor moiety and the acceptor moiety are in a suitable juxtaposition to yield a BRET signal when L is bound to BP, and wherein NADPH-induced binding of L to BP results in an increase in BRET efficiency.

2. The sensor molecule according to claim 1, wherein said heterologous protein domain further comprises a fluorescent protein, a self-labelling protein tag conjugated to a fluorophore, or a protein domain comprising an unnatural amino acid conjugated to a fluorophore.

3. The sensor molecule according to claim 1, wherein said luciferase enzyme is selected from the group consisting of a circular permutated luciferase, *Renilla* luciferase, firefly luciferase, *Gaussia* luciferase, and mutants thereof.

4. The sensor molecule according to claim 1, wherein the linker is a flexible polypeptide of at least 5 Gly residues.

5. The sensor molecule according to claim 1, wherein said L is selected from the group consisting of trimethoprim, methotrexate, aminopterin and 2,4 diamino-N10-methylpteroic acid (DAMPA).

6. The sensor molecule according to claim 1, wherein the sensor molecule is immobilized or absorbed to a solid carrier.

7. A method for fluorescence or luminescence-based in vitro detection of a concentration of NADPH in a sample, the method comprising (a) contacting the sample with a sensor molecule according to claim 1 under conditions allowing for an NADPH-dependent binding of said L to BP; and (b) analyzing a change in a signal generated by modulation of the spectroscopic properties of the fluorescence acceptor moiety or emission spectra of the sensor molecule and relating the signal change to the concentration of NADPH in the sample.

8. The method according to claim 7, wherein the sample is a biological sample or a fraction thereof.

9. The method according to claim 7, wherein the sample is contacted with the sensor molecule while the sensor molecule is immobilized or absorbed onto a solid carrier.

10. A kit of parts comprising the sensor molecule according to claim 1 and a solid carrier.

11. The kit according to claim 10, further comprising a luciferase substrate.

12. The kit according to claim 10 further comprising instructions or at least one further component suitable for one or more of the following:
  (i) ex vivo clinical or diagnostic testing performed on a serum or bodily fluid sample;
  (ii) an ex vivo enzymatic assay that involves formation or consumption of NADPH;
  (iii) ex vivo high-throughput screening for compounds that can modulate NADPH in cells or for validation of a toxicity profile of a therapeutic drug;
  (iv) live cell measurements comprising use of a widefield fluorescence microscope, confocal fluorescence microscope or a Fluorescence Lifetime Imaging Microscopy (FLIM) system with appropriate excitation and emission filters.

13. The sensor molecule according to claim 1, wherein said DHFR is a variant of SEQ ID NO:2 having at least 95% sequence identity to SEQ ID NO:2 and comprising one or more mutations selected from the group consisting of R98A, R44A and H45Q compared to SEQ ID NO:2.

14. The sensor molecule according to claim 6, wherein the solid carrier is selected from the group consisting of glass, a transparent plastic, a gold surface, a membrane, paper and a gel.

15. The method according to claim 8, wherein the sample is a cell lysate or a bodily fluid.

16. The kit of parts according to claim 10, wherein said solid carrier is paper or a transparent object.

17. The sensor molecule according to claim 1, wherein the acceptor moiety is a fluorophore.

18. The sensor molecule according to claim 1, wherein the acceptor moiety is a tethered fluorophore.

19. The sensor molecule according the claim 1, wherein the acceptor moiety is selected from the group consisting of cyanine dyes, fluorescent proteins, rhodamine dyes, fluorescein derivatives, triarylmethane dyes, naphthalimide dyes, xanthene dyes, acridine dyes, and coumarins.

20. The sensor molecule according to claim 1, wherein said heterologous protein domain is inserted at or replacing at least part of the region corresponding to positions 23 to 24 of *E. coli* DHFR.

* * * * *